Figure 1:
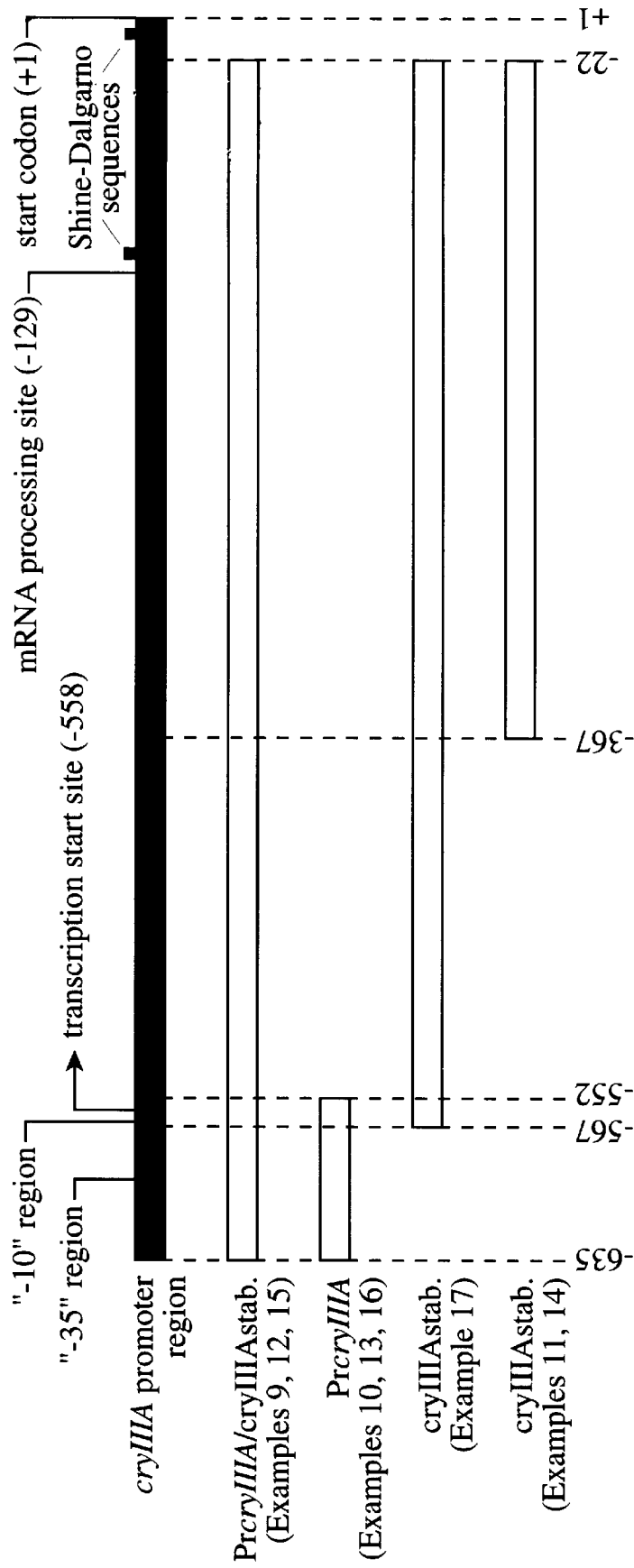

United States Patent [19]
Widner et al.

[11] Patent Number: 5,955,310
[45] Date of Patent: Sep. 21, 1999

[54] METHODS FOR PRODUCING A POLYPEPTIDE IN A BACILLUS CELL

[75] Inventors: William Widner; Alan Sloma; Michael D. Thomas, all of Davis, Calif.

[73] Assignee: Novo Nordisk Biotech, Inc., Davis, Calif.

[21] Appl. No.: 09/031,442

[22] Filed: Feb. 26, 1998

[51] Int. Cl.$^6$ .............................. C12P 21/06; C12N 9/00; C12N 1/20; C12N 9/88

[52] U.S. Cl. ..................... 435/69.1; 435/183; 435/194; 435/252.31; 435/232; 233/199; 233/205; 233/195; 233/209

[58] Field of Search ..................................... 435/69.1, 183, 435/194, 252.31, 233, 232, 199, 205, 195, 209

[56] References Cited

FOREIGN PATENT DOCUMENTS

WO 94/25612   11/1994   WIPO .

OTHER PUBLICATIONS

Agaisse et al., Molecular Biology, 13 (1), pp. 97–107, (1994).
Hue et al., Journal of Bacteriology, vol. 177, No. 12, pp. 3465–3471, (1995).
Ichikawa et al., FEMS Microbiology Letters, 111, pp. 219–224, (1993).

*Primary Examiner*—Robert A. Wax
*Assistant Examiner*—Maryam Monshipouri
*Attorney, Agent, or Firm*—Steve T. Zelson; Robert L. Starnes

[57] ABSTRACT

The present invention relates to methods for producing a polypeptide, comprising: (a) cultivating a Bacillus host cell in a medium conducive for the production of the polypeptide, wherein the Bacillus cell comprises a nucleic acid construct comprising (i) a tandem promoter in which each promoter sequence of the tandem promoter is operably linked to a single copy of a nucleic acid sequence encoding the polypeptide and (ii) an mRNA processing/stabilizing sequence located downstream of the tandem promoter and upstream of the nucleic acid sequence encoding the polypeptide; and (b) isolating the polypeptide from the cultivation medium. The present invention also relates to Bacillus cells for producing a polypeptide comprising a nucleic acid construct which comprises (i) a tandem promoter in which each promoter sequence of the tandem promoter is operably linked to a single copy of a nucleic acid sequence encoding the polypeptide and (ii) an mRNA processing/stabilizing sequence located downstream of the tandem promoter and upstream of the nucleic acid sequence encoding the polypeptide.

32 Claims, 20 Drawing Sheets

METHODS FOR PRODUCING A POLYPEPTIDE IN A BACILLUS CELL

BACKGROUND OF THE INVENTION

1. Field of the Invention

The present invention relates to methods for producing a polypeptide in a bacterial cell.

2. Description of the Related Art

Bacilli are well established as host cell systems for the production of native and recombinant proteins. However, Bacillus host cells with the desirable traits of increased protein expression may not necessarily have the most desirable characteristics for commercial use.

Conventionally, maximal expression of a gene contained in a Bacillus cell is achieved by amplifying in the chromosome an expression cassette containing a single promoter operably linked to a gene of interest and an amplifiable selectable marker gene, e.g., an antibiotic resistance marker. The amplification leads to the production of multiple copies of the expression cassette and the selectable marker gene in the chromosome.

However, there are disadvantages associated with this approach. For example, it may not be possible to achieve saturating levels of mRNA by amplifying genes driven by single promoters. Also, the production of multiple copies of the expression cassette and the selectable marker gene in the chromosome of a cell may not be stable. Furthermore, the removal of the selectable marker genes without also losing the expression cassettes may not be technically feasible.

Ichikawa et al. (1993, *FEMS Microbiological Letters* 111: 219–224) disclose the extracellular production of cholera toxin B in *Bacillus brevis* containing an expression-secretion vector with multiple promoters which mediate the expression of the gene encoding the mature cholera toxin B.

Agaisse and Lereclus (1994, *Molecular Microbiology* 13:97–107) disclose a structural and functional analysis of the promoter region involved in the full expression of the cryIIIA toxin gene of *Bacillus thuringiensis*. WO 94/25612 discloses an mRNA stabilizer region downstream of the promoter and upstream of the coding sequence of the cryIIIA gene which increases expression of the gene.

Hue et al. (1995, *Journal of Bacteriology* 177:3465–3471) disclose a 5' mRNA stabilizer sequence which stabilized several heterologous RNA sequences when present at the 5' end and increased expression of downstream coding sequences several-fold in *Bacillus subtilis*.

It is an object of the present invention to provide improved methods for producing a polypeptide in a Bacillus strain.

SUMMARY OF THE INVENTION

The present invention relates to methods for producing a polypeptide, comprising: (a) cultivating a Bacillus host cell in a medium conducive for the production of the polypeptide, wherein the Bacillus cell comprises a nucleic acid construct comprising (i) a tandem promoter in which each promoter sequence of the tandem promoter is operably linked to a single copy of a nucleic acid sequence encoding the polypeptide and (ii) an mRNA processing/stabilizing sequence located downstream of the tandem promoter and upstream of the nucleic acid sequence encoding the polypeptide; and (b) isolating the polypeptide from the cultivation medium.

The present invention also relates to Bacillus cells comprising a nucleic acid construct which comprises (i) a tandem promoter in which each promoter sequence of the tandem promoter is operably linked to a single copy of a nucleic acid sequence encoding a polypeptide and (ii) an mRNA processing/stabilizing sequence located downstream of the tandem promoter and upstream of the nucleic acid sequence encoding the polypeptide.

BRIEF DESCRIPTION OF THE FIGURES

FIG. 1 shows a map of the cryIIIA promoter and the cryIIIA processing/stabilizing sequence.

FIG. 2 shows schematically various constructions containing a tandem promoter and the cryIIIA mRNA processing/stabilizing sequence.

FIG. 3 shows a restriction map of pDG268MCS.

FIG. 4 shows a restriction map of pDG268MCSΔ-$Pr_{CryIIIA}$/cryIIIAstab/SAV.

FIG. 5 shows a restriction map of pDG268MCSΔneo-$Pr_{cryIIIA}$/CryIIIAstab/SAV.

FIG. 6 shows a restriction map of pHP13amp-MCS.

FIG. 7 shows a restriction map of pSX222.

FIG. 8 shows a restriction map of pHP13amp-SAV.

FIG. 9 shows a restriction map of pDG268MCS-$Pr_{amyL}$/SAV.

FIG. 10 shows a restriction map of pDG268MCS-$Pr_{amyQ}$/SAV.

FIG. 11 shows a restriction map of pUC18-$Pr_{cryIIIA}$/cryIIIAstab/cryIIIA.

FIG. 12 shows a restriction map of pDG268MCS-$Pr_{cryIIIA}$/cryIIIAstab/SAV.

FIG. 13 shows a restriction map of pDG268MCSΔneo-$Pr_{cryIIIA}$/SAV.

FIG. 14 shows a restriction map of pDG268MCS-$Pr_{amyL}$/cryIIIAstab/SAV.

FIG. 15 shows a restriction map of pDG268MCSΔneo-$Pr_{amyL}$/$Pr_{CryIIIA}$/cryIIIAstab/SAV.

FIG. 16 shows a restriction map of pDG268MCSΔneo-$Pr_{amyL}$/$Pr_{cryIIIA}$/SAV.

FIG. 17 shows a restriction map of pDG268MCSΔneo-$Pr_{amyQ}$/cryIIIAstab/SAV.

FIG. 18 shows a restriction map of pDG268MCS-$Pr_{amyQ}$/$Pr_{cryIIIA}$/cryIIIAstab/SAV.

FIG. 19 shows a restriction map of pDG268MCSΔneo-$Pr_{amyQ}$/$Pr_{cryIIIA}$/SAV.

FIG. 20 shows a restriction map of pDG268MCSΔneo-cryIIIAstab/SAV.

DETAILED DESCRIPTION OF THE INVENTION

The present invention relates to methods for producing a polypeptide, comprising: (a) cultivating a Bacillus cell in a medium conducive for the production of the polypeptide, wherein the Bacillus cell comprises a nucleic acid construct comprising (i) a tandem promoter in which each promoter sequence of the tandem promoter is operably linked to a single copy of a nucleic acid sequence encoding the polypeptide and (ii) an mRNA processing/stabilizing sequence located downstream of the tandem promoter and upstream of the nucleic acid sequence encoding the polypeptide; and (b) isolating the polypeptide from the cultivation medium.

"Promoter" is defined herein as a nucleic acid sequence involved in the binding of RNA polymerase to initiate transcription of a gene. "Tandem promoter" is defined herein as two or more promoter sequences each of which is operably linked to a coding sequence and mediates the transcription of the coding sequence into mRNA. "Operably linked" is defined herein as a configuration in which a control sequence, e.g., a promoter sequence, is appropriately placed at a position relative to a coding sequence such that the control sequence directs the production of a polypeptide encoded by the coding sequence. "Coding sequence" is defined herein as a nucleic acid sequence which is transcribed into mRNA and translated into a polypeptide when placed under the control of the appropriate control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence.

Each promoter sequence of the tandem promoter may be any nucleic acid sequence which shows transcriptional activity in the Bacillus cell of choice including a mutant, truncated, and hybrid promoter, and may be obtained from genes encoding extracellular or intracellular polypeptides either homologous or heterologous to the Bacillus cell. Each promoter sequence may be native or foreign to the nucleic acid sequence encoding the polypeptide and native or foreign to the Bacillus cell. The promoter sequences may be the same promoter sequence or different promoter sequences.

In a preferred embodiment, the promoter sequences may be obtained from a bacterial source. In a more preferred embodiment, the promoter sequences may be obtained from a gram positive bacterium such as a Bacillus strain, e.g., *Bacillus alkalophilus, Bacillus amyloliquefaciens, Bacillus brevis, Bacillus circulars, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or a Streptomyces strain, e.g., *Streptomyces lividans* or *Streptomyces murinus*; or from a gram negative bacterium, e.g., *E. coli* or Pseudomonas sp.

An example of a suitable promoter for directing the transcription of a nucleic acid sequence in the methods of the present invention is the promoter obtained from the *E. coli* lac operon. Another example is the promoter of the *Streptomces coelicolor* agarase gene (dagA). Another example is the promoter of the *Bacillus lentus* alkaline protease gene (aprH). Another example is the promoter of the *Bacillus licheniformis* alkaline protease gene (subtilisin Carlsberg gene). Another example is the promoter of the *Bacillus subtilis* levansucrase gene (sacB). Another example is the promoter of the *Bacillus licheniformis* alpha-amylase gene (amyL). Another example is the promoter of the *Bacillus stearothermophilus* maltogenic amylase gene (amyM). Another example is the promoter of the *Bacillus amyloliquefaciens* alpha-amylase gene (amyQ). Another example is the promoter of the *Bacillus licheniformis* penicillinase gene (penP). Another example are the promoters of the *Bacillus subtilis* xylA and xylB genes. Another example is the promoter of the *Bacillus thuringiensis* subsp. *tenebrionis* CryIIIA gene (cryIIIA, SEQ ID NO:21). Another example is the promoter of the prokaryotic beta-lactamase gene (Villa-Kamaroff et al., 1978, *Proceedings of the National Academy of Sciences USA* 75:3727–3731). Another example is the promoter of the spol bacterial phage promoter. Another example is the tac promoter (DeBoer et al., 1983, *Proceedings of the National Academy of Sciences USA* 80:21–25).

Further promoters are described in "Useful proteins from recombinant bacteria" in *Scientific American,* 1980, 242:74–94; and in Sambrook, Fritsch, and Maniatus, 1989, *Molecular Cloning, A Laboratory Manual,* 2d edition, Cold Spring Harbor, N.Y.

The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the Bacillus cell.

In a preferred embodiment, the tandem promoter contains at least the amyQ promoter of the *Bacillus amyloliquefaciens* alpha-amylase gene. In another preferred embodiment, the tandem promoter contains at least the amyL promoter of the *Bacillus licheniformis* alpha-amylase gene. In another preferred embodiment, the tandem promoter contains at least the cryIIIA promoter (Agaisse and Lereclus, 1994, supra).

In a more preferred embodiment, the tandem promoter contains at least the amyL promoter and the cryIIIA promoter. In another more preferred embodiment, the tandem promoter contains at least the amyQ promoter and the cryIIIA promoter. In another more preferred embodiment, the tandem promoter contains at least two copies of the amyL promoter. In another more preferred embodiment, the tandem promoter contains at least two copies of the amyQ promoter. In another more preferred embodiment, the tandem promoter contains at least two copies of the cryIIIA promoter.

"An mRNA processing/stabilizing sequence" is defined herein as a sequence located downstream of one or more promoter sequences and upstream of a coding sequence to which each of the one or more promoter sequences are operably linked such that all mRNAs synthesized from each promoter sequence may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, supra). The mRNA processing/stabilizing sequence is complementary to the 3' extremity of a bacterial 16S ribosomal RNA. In a preferred embodiment, the mRNA processing/stabilizing sequence generates essentially single-size transcripts with a stabilizing sequence at the 5' end of the transcripts.

In a more preferred embodiment, the mRNA processing/stabilizing sequence is the *Bacillus thuringiensis* cryIIIA mRNA processing/stabilizing sequence disclosed in WO 94/25612 and Agaisse and Lereclus, 1994, supra, or portions thereof which retain the mRNA processing/stabilizing function. In another more preferred embodiment, the mRNA processing/stabilizing sequence is the *Bacillus subtilis* SP82 mRNA processing/stabilizing sequence disclosed in Hue et al., 1995, supra, or portions thereof which retain the mRNA processing/stabilizing function.

Figure 2:
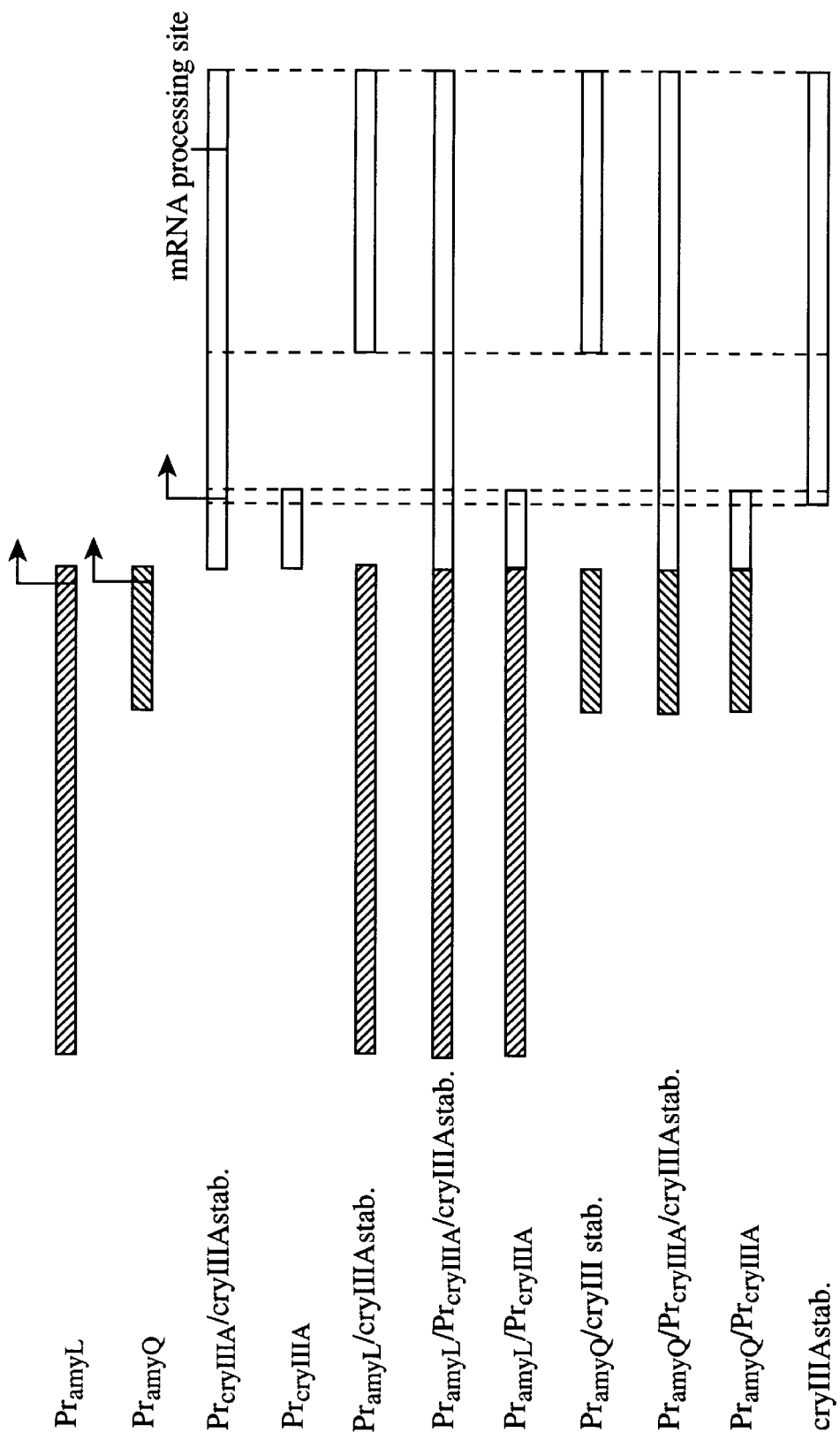

When the cryIIIA promoter and its mRNA processing/stabilizing sequence are employed in the methods of the present invention, a DNA fragment containing the sequence disclosed in WO 94/25612 and Agaisse and Lereclus, 1994, supra, delineated by nucleotides −635 to −22 (FIG. 1) (SEQ ID NO:21), or portions thereof which retain the promoter and mRNA processing/stabilizing functions, may be used. The cryIIIA promoter is delineated by nucleotides −635 to −552 while the cryIIIA mRNA processing/stabilizing sequence is contained within nucleotides −551 to −22. Furthermore, DNA fragments containing only the cryIIIA promoter or only the cryIIIA mRNA processing/stabilizing sequence may be prepared using methods well known in the art to construct various tandem promoter and mRNA processing/stabilizing sequence combinations. In this embodiment, the cryIIIA promoter and its mRNA processing/stabilizing sequence are preferably placed downstream of the other promoter sequence(s) constituting the tandem promoter and upstream of the coding sequence of the gene of interest. Various constructions containing a tandem promoter and the cryIIIA mRNA processing/stabilizing sequence are shown in FIG. 2.

The Bacillus cell may contain one or more copies of the nucleic acid construct. In a preferred embodiment, the Bacillus cell contains a single copy of the nucleic acid construct.

The nucleic acid construct may further contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

A particular advantage of the present invention is that a Bacillus cell can be produced free of a selectable marker gene, i.e., after the introduction of the nucleic acid construct into the Bacillus cell, the selectable marker gene can be deleted from the Bacillus cell making the cell marker-free. The nucleic acid construct containing a single copy of the nucleic acid sequence encoding the polypeptide allows for the removal of the selectable marker gene to produce a Bacillus cell free of such a marker which may be preferable for regulatory and environmental reasons.

Gene deletion or replacement techniques may be used for the complete removal of the selectable marker gene. In such methods, the deletion of the selectable marker gene may be accomplished by homologous recombination using a plasmid which has been constructed to contiguously contain the 5' and 3' regions flanking the selectable marker gene. The contiguous 5' and 3' regions may be introduced into a Bacillus cell on a temperature-sensitive plasmid, e.g., pE 194, in association with a second selectable marker at a permissive temperature to allow the plasmid to become established in the cell. The cell is then shifted to a non-permissive temperature to select for cells which have the plasmid integrated into the chromosome at one of the homologous flanking regions. Selection for integration of the plasmid is effected by selection for the second selectable marker. After integration, the second integration event is stimulated by shifting the cells to the permissive temperature for several generations without selection. The cells are plated to obtain single colonies and the colonies are examined for loss of both selectable markers (see, for example, Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C., 1993).

The polypeptide may be any polypeptide whether native or heterologous to the Bacillus cell. The term "polypeptide" is not meant herein to refer to a specific length of the encoded product and, therefore, encompasses peptides, oligopeptides, and proteins. The polypeptide may also be a naturally occurring allelic or engineered variant of a polypeptide.

Preferably, the polypeptide is a hormone, a hormone variant, an enzyme, a receptor or a portion thereof, an antibody or a portion thereof, or a reporter. In a more preferred embodiment, the polypeptide is an oxidoreductase. In another more preferred embodiment, the polypeptide is a transferase. In another more preferred embodiment, the polypeptide is a hydrolase. In another more preferred embodiment, the polypeptide is a lyase. In another more preferred embodiment, the polypeptide is an isomerase. In another more preferred embodiment, the polypeptide is a ligase.

In an even more preferred embodiment, the polypeptide is an aminopeptidase. In another even more preferred embodiment, the polypeptide is an amylase. In another even more preferred embodiment, the polypeptide is a carbohydrase. In another even more preferred embodiment, the polypeptide is a carboxypeptidase. In another even more preferred embodiment, the polypeptide is a catalase. In another even more preferred embodiment, the polypeptide is a cellulase. In another even more preferred embodiment, the polypeptide is a chitinase. In another even more preferred embodiment, the polypeptide is a cutinase, In another even more preferred embodiment, the polypeptide is a cyclodextrin glycosyltransferase. In another even more preferred embodiment, the polypeptide is a deoxyribonuclease. In another even more preferred embodiment, the polypeptide is an esterase. In another even more preferred embodiment, the polypeptide is an alpha-galactosidase. In another even more preferred embodiment, the polypeptide is a beta-galactosidase. In another even more preferred embodiment, the polypeptide is a glucoamylase. In another even more preferred embodiment, the polypeptide is an alpha-glucosidase. In another even more preferred embodiment, the polypeptide is a beta-glucosidase. In another even more preferred embodiment, the polypeptide is a beta-glucosidase. In another even more preferred embodiment, the polypeptide is a laccase. In another even more preferred embodiment, the polypeptide is a lipase. In another even more preferred embodiment, the polypeptide is a mannosidase. In another even more preferred embodiment, the polypeptide is a mutanase. In another even more preferred embodiment, the polypeptide is an oxidase. In another even more preferred embodiment, the polypeptide is a pectinolytic enzyme. In another even more preferred embodiment, the polypeptide is a peroxidase. In another even more preferred embodiment, the polypeptide is a phytase. In another even more preferred embodiment, the polypeptide is a polyphenoloxidase. In another even more preferred embodiment, the polypeptide is a proteolytic enzyme. In another even more preferred embodiment, the polypeptide is a ribonuclease. In another even more preferred embodiment, the polypeptide is a transglutaminase. In another even more preferred embodiment, the polypeptide is a xylanase.

In a most preferred embodiment, the polypeptide is a serine protease, for example, a subtilisin. In another most preferred embodiment, the polypeptide is a maltogenic amylase. In another most preferred embodiment, the polypeptide is a pullulanase.

The methods of the present invention may also be used for the recombinant production of polypeptides which are native to the Bacillus cell. The present invention also encompasses, within the scope of the term "heterologous polypeptide", such recombinant production of native polypeptides, to the extent that such expression involves the use of genetic elements not native to the Bacillus cell, or use of native elements which have been manipulated to function in a manner not normally occurring in the host cell.

In the methods of the present invention, heterologous polypeptides may also include fused or hybrid polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the Bacillus cell.

The construction of a Bacillus cell comprising a tandem promoter and an mRNA processing/stabilizing sequence operably linked to a nucleic acid sequence encoding a polypeptide of interest may be accomplished by modifying an isolated nucleic acid sequence encoding the polypeptide using methods well known in the art to operably link the tandem promoter and the mRNA processing/stabilizing sequence to the nucleic acid sequence, inserting the modified sequence into a vector, and introducing the vector into the Bacillus cell's chromosome by homologous recombination or into the Bacillus cell as an extrachromosomal autonomously replicating element, e.g., plasmid. However, it will be understood that the nucleic acid sequence may also be manipulated in vivo in the Bacillus cell using methods well known in the art.

In the methods of the present invention, a nucleic acid sequence encoding a polypeptide of interest may be native or foreign to the Bacillus cell. A foreign nucleic acid sequence encoding a heterologous polypeptide may be obtained from any prokaryotic, eukaryotic, or other source, e.g., archaebacteria. In a preferred embodiment, the nucleic acid sequence is obtained from a bacterial strain, such as a gram-negative or a gram-positive bacterial cell. In a more preferred embodiment, the nucleic acid sequence encoding the polypeptide is obtained from a Bacillus cell. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide are known in the art and include, for example, isolation from genomic DNA, preparation from cDNA, or a combination thereof. The cloning of the nucleic acid sequences from such genomic DNA can be effected, e.g., by using antibody screening of expression libraries to detect cloned DNA fragments with shared structural features or the well known polymerase chain reaction (PCR). See, for example, Innis et al., 1990, *PCR Protocols: A Guide to Methods and Application*, Academic Press, New York. Other nucleic acid amplification procedures such as ligase chain reaction (LCR), ligated activated transcription (LAT), and nucleic acid sequence-based amplification (NASBA) may be used. The cloning procedures may involve excision and isolation of a desired nucleic acid fragment comprising the nucleic acid sequence encoding the polypeptide, insertion of the fragment into a vector molecule, and incorporation of the recombinant vector into a Bacillus cell where clones of the nucleic acid sequence will be replicated. The nucleic acid sequence may be of genomic, cDNA, RNA, semisynthetic, synthetic origin, or any combinations thereof.

An isolated nucleic acid sequence encoding a polypeptide of interest may then be manipulated to produce a nucleic acid construct by operably linking the nucleic acid sequence to a tandem promoter and to an mRNA processing/stabilizing sequence as well as one or more additional control sequences which direct the expression of the coding sequence in a Bacillus cell under conditions compatible with the control sequences. Expression will be understood to include any step involved in the production of the polypeptide including, but not limited to, transcription, post-transcriptional modification, translation, post-translational modification, and secretion. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. In addition to the tandem promoter described earlier, such control sequences include, but are not limited to, a leader, a signal sequence, and a transcription terminator. The control sequences may be provided with linkers for the purpose of introducing specific restriction sites facilitating ligation of the control sequences with the coding region of the nucleic acid sequence encoding a polypeptide.

The control sequence may also be a suitable transcription terminator sequence, a sequence recognized by a Bacillus cell to terminate transcription. The terminator sequence is operably linked to the 3' terminus of the nucleic acid sequence encoding the polypeptide. Any terminator which is functional in the Bacillus cell of choice may be used in the present invention.

The control sequence may also be a suitable leader sequence, a nontranslated region of an mRNA which is important for translation by the Bacillus cell. The leader sequence is operably linked to the 5' terminus of the nucleic acid sequence encoding the polypeptide. Any leader sequence which is functional in the Bacillus cell of choice may be used in the present invention.

The control sequence may also be a signal peptide coding region, which codes for an amino acid sequence linked to the amino terminus of the polypeptide which can direct the expressed polypeptide into the cell's secretory pathway. The signal peptide coding region may be native to the polypeptide of the invention or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a Bacillus species. However, any signal peptide coding region capable of directing the expressed polypeptide into the secretory pathway of a Bacillus cell of choice may be used in the present invention.

An effective signal peptide coding region for Bacillus cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109–137.

In the methods of the present invention, a recombinant expression vector comprising a nucleic acid sequence encoding a polypeptide of interest, a tandem promoter and an mRNA processing/stabilizing sequence, and transcriptional and translational stop signals may be used for the recombinant production of a polypeptide. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence may be expressed by inserting the nucleic acid sequence or a nucleic acid construct comprising the sequence into an appropriate vector for expression. In creating the expression vector, the coding sequence is located in the vector so that the coding sequence is operably linked with a tandem promoter and an mRNA processing/stabilizing sequence and any other appropriate control sequences for expression, and possibly secretion.

The recombinant expression vector may be any vector which can be conveniently subjected to recombinant DNA procedures and can bring about the expression of the nucleic acid sequence on introduction into a Bacillus cell. The choice of the vector will typically depend on the compatibility of the vector with the Bacillus cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the Bacillus cell, is integrated into the genome and replicated together with the chromosome(s) into which it has been integrated. The vector system may be a single vector or plasmid or two or more vectors or plasmids, or a transposon.

"Introduction" means introducing a vector comprising the nucleic acid sequence into a Bacillus cell so that the vector is maintained as a chromosomal integrant or as a self-replicating extrachromosomal vector. Integration is generally considered to be an advantage as the nucleic acid sequence is more likely to be stably maintained in the cell. Integration of the vector into the chromosome occurs by homologous recombination, non-homologous recombination, or transposition.

The introduction of an expression vector into a Bacillus cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnau and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thorne, 1987, *Journal of Bacteriology* 169:5271–5278).

For integration, the vector may rely on the nucleic acid sequence encoding the polypeptide or any other element of the vector for stable integration of the vector into the genome by homologous recombination. Alternatively, the vector may contain additional nucleic acid sequences for directing integration by homologous recombination into the genome of the Bacillus cell. The additional nucleic acid sequences enable the vector to be integrated into the Bacillus cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the Bacillus cell. Furthermore, the integrational elements may be non-encoding or encoding nucleic acid sequences.

For autonomous replication, the vector may further comprise an origin of replication enabling the vector to replicate autonomously in the Bacillus cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. The origin of replication may be one having a mutation to make its function temperature-sensitive in the Bacillus cell (see, e.g., Ehrlich, 1978, *Proceedings of the National Academy of Sciences USA* 75:1433).

The procedures used to ligate the elements described above to construct the recombinant expression vectors of the present invention are well known to one skilled in the art (see, e.g., Sambrook et al, 1989, supra).

In the methods of the present invention, the Bacillus cell may be a wild-type Bacillus cell or a mutant thereof. Furthermore, the Bacillus cell may be an alkalophilic or a thermophilic Bacillus. In a preferred embodiment, the Bacillus cell is a *Bacillus alkalophilus* cell. In another preferred embodiment, the Bacillus cell is a *Bacillus amyloliquefaciens* cell. In another preferred embodiment, the Bacillus cell is a *Bacillus brevis* cell. In another preferred embodiment, the Bacillus cell is a *Bacillus circulans* cell. In another preferred embodiment, the Bacillus cell is a *Bacillus clausii* cell. In another preferred embodiment, the Bacillus cell is a *Bacillus coagulans* cell. In another preferred embodiment, the Bacillus cell is a *Bacillus firmus* cell. In another preferred embodiment, the Bacillus cell is a *Bacillus lautus* cell. In another preferred embodiment, the Bacillus cell is a *Bacillus lentus* cell. In another preferred embodiment, the Bacillus cell is a *Bacillus licheniformis* cell. In another preferred embodiment, the Bacillus cell is a

*Bacillus megaterium* cell. In another preferred embodiment, the Bacillus cell is a *Bacillus pumilus* cell. In another preferred embodiment, the Bacillus cell is a *Bacillus stearothermophilus* cell. In another preferred embodiment, the Bacillus cell is a *Bacillus subtilis* cell. In another preferred embodiment, the Bacillus cell is a *Bacillus thuringiensis* cell.

In the methods of the present invention, the Bacillus cell may be a recombinant cell comprising, for example, a nucleic acid sequence encoding a heterologous polypeptide.

The cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium.

The polypeptides may be detected using methods known in the art that are specific for the polypeptides. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

In the methods of the present invention, the Bacillus cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a Bacillus cell containing only one of the promoter sequences of the tandem promoter operably linked to a nucleic acid sequence encoding the polypeptide when cultured under identical production conditions.

The resulting polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J.-C. Janson and Lars Ryden, editors, VCH Publishers, New York, 1989).

The present invention also relates to Bacillus cells comprising two or more promoters operably linked in tandem to a nucleic acid sequence encoding a polypeptide and an mRNA processing/stabilizing sequence located downstream of the tandem promoter and upstream of the nucleic acid sequence encoding the polypeptide. In a preferred embodiment, the Bacillus cell is free of a selectable marker gene.

The present invention also relates to methods for obtaining a Bacillus host cell, comprising introducing into a Bacillus cell a nucleic acid construct comprising (i) a tandem promoter in which each promoter sequence of the tandem promoter is operably linked to a single copy of a nucleic acid sequence encoding a polypeptide and (ii) an mRNA processing/stabilizing sequence located downstream of the tandem promoter and upstream of the nucleic acid sequence encoding the polypeptide.

The present invention further relates to methods for producing a selectable marker-free mutant of a Bacillus cell, comprising deleting a selectable marker gene of the Bacillus cell, wherein the Bacillus cell comprises a nucleic acid construct comprising (i) a tandem promoter in which each promoter sequence of the tandem promoter is operably linked to a single copy of a nucleic acid sequence encoding a polypeptide and (ii) an mRNA processing/stabilizing sequence located downstream of the tandem promoter and upstream of the nucleic acid sequence encoding the polypeptide.

The present invention is further described by the following examples which should not be construed as limiting the scope of the invention.

EXAMPLES

Bacterial Strains

*E. coli* DH5α, *E. coli* JM101, and *Bacillus subtilis* PL1801IIE (amyE, apr, npr, spoIIE::Tn917).

Primers and Oligos

All primers and oligos were synthesized on an Applied Biosystems Model 394 Synthesizer (Applied Biosystems, Inc., Foster City, Calif.) according to the manufacturer's instructions.

Example 1

Construction of Plasmid pDG268MCS pDG268 (Antoniewski, et al., 1990, *Journal of Bacteriology* 172:86–93) was digested with Tth111I and EcoRI, and the digest was subjected to electrophoresis using a 0.7% agarose gel with 45 mM Tris-borate-1 mM EDTA (TBE). The largest plasmid fragment of approximately 6020 bp was excised from the gel and the DNA was recovered using the Qiaquick DNA purification kit (Qiagen, Inc., Chatsworth, Calif.) according to the manufacturer's instructions. The recovered DNA was then ligated with the following synthetic polylinker shown below to introduce unique SfiI and BamHI sites into the plasmid.

```
           SfiI ApaISmaI  AatII HINDIII ClaI    BamHI    NotI

5'-AATTGGCCTTAAGGGCCCGGGACGTCAAGCTTATCGATGCGGATCCGCGGCCGC-3'

3'-CCGGAATTCCCGGGCCCTGCAGTTCGAATAGCTACGCCTAGGCGCCGGCGC-5'  (SEQ ID NOs:1
                                                           and 2, respectively)
```

Figure 3:
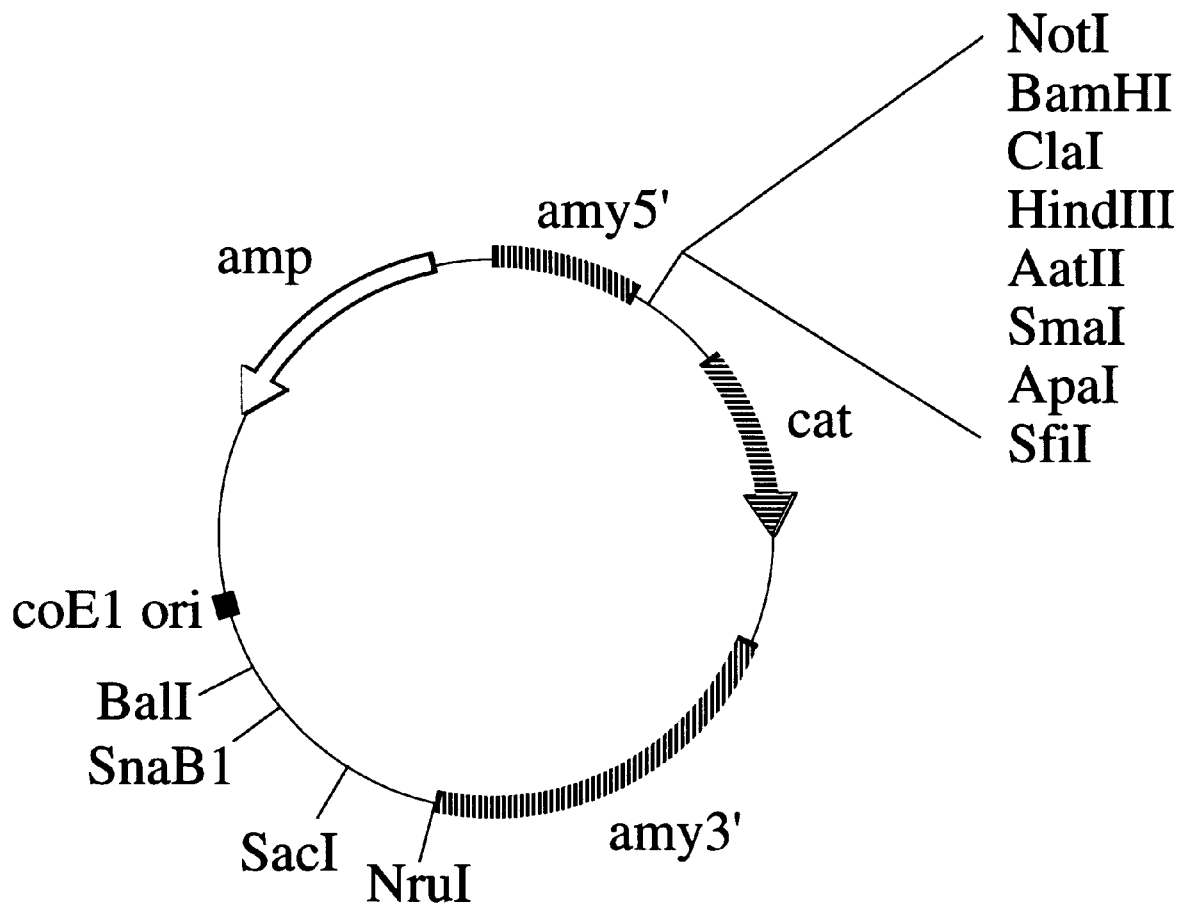

*E. coli* DH5α was transformed with the ligation mixture and ampicillin resistant transformants were selected on LB plates supplemented with 100 μg of ampicillin per ml. Plasmid DNA was purified according to Sambrook et al., 1989, supra, and digested with SfiI and NotI to identify plasmids which contained these sites and by implication, the polylinker shown above (pDG268 does not contain these two restriction sites). Several plasmids were identified which contained both restriction sites and in addition were approximately 3.0 kb smaller than pDG268 as a result of replacing the lacZ gene of pDG268 with the synthetic polylinker. One such plasmid was chosen and designated pDG268MCS (MCS refers to multiple cloning site) (FIG. 3).

Figure 4:
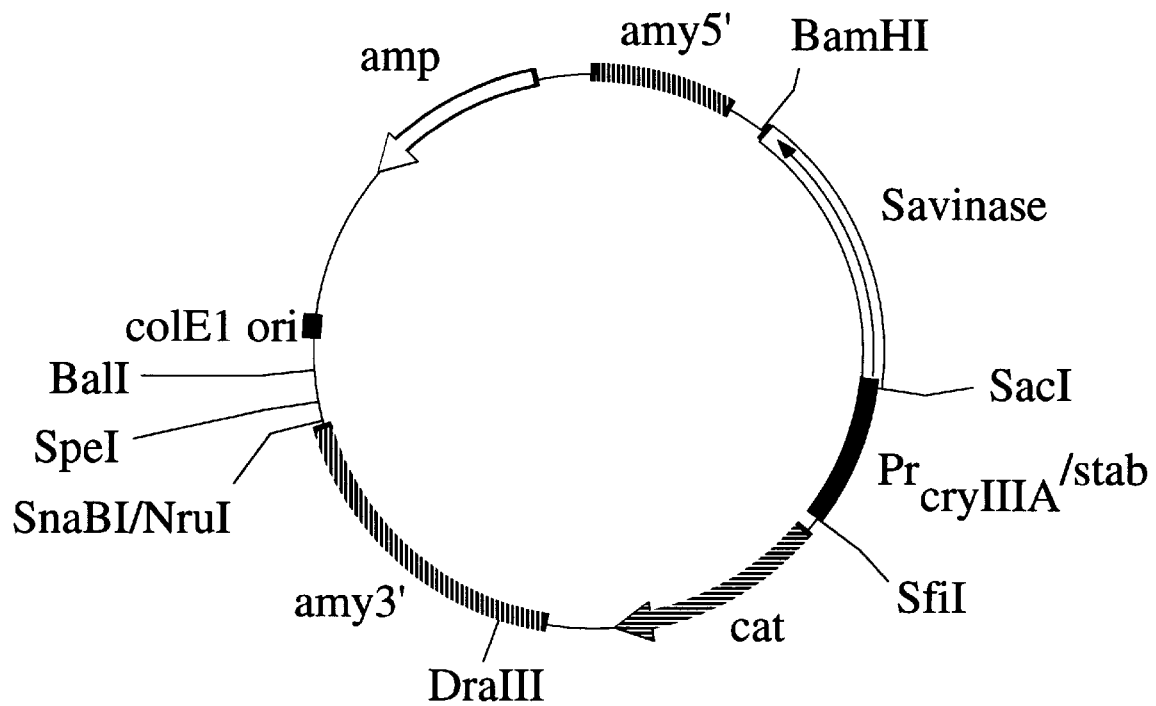
Figure 12:
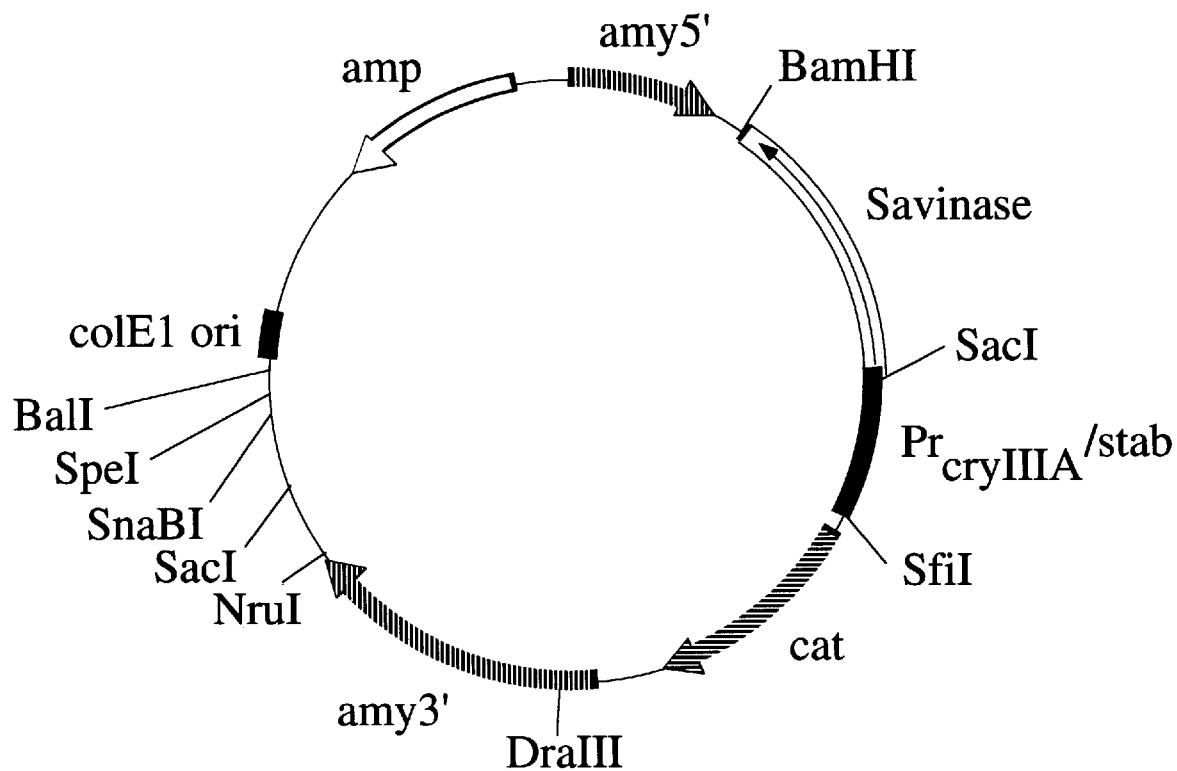

Example 2
Construction of pDG268MCSΔ-Pr$_{cryIIIA}$/cryIIIAstab/SAV pDG268MCSΔ-Pr$_{cryIIIA}$/cryIIIAstab/SAV was constructed to delete the SacI site in pDG268MCS of Example 1 to facilitate the swapping of promoter fragments engineered to contain a SacI site at their 3' end. pDG268MCS-Pr$_{cryIIIA}$/cryIIIAstab/SAV (see Example 9 and FIG. 12) was digested with SnaBI and NruI (both restriction sites flank the SacI site of the vector), ligated, and transformed into E. coli DH5α. Ampicillin resistant transformants were selected on LB plates supplemented with 100 μg of ampicillin per ml. Plasmid DNA was purified from several transformants and recovered as described in Example 1. The plasmid DNA was digested with SacI to identify plasmids which were deleted for the SacI site located in the vector sequence and thus cleaved only once due to the SacI site downstream of the cryIIIA promoter. Such a plasmid was identified and designated pDG268MCSΔ-Pr$_{cryIIIA}$/cryIIIAstab/SAV (FIG. 4).

Example 3
Construction of pDG268MCSΔneo-Pr$_{cryIIIA}$/cryIIIAstab/SAV

Figure 5:
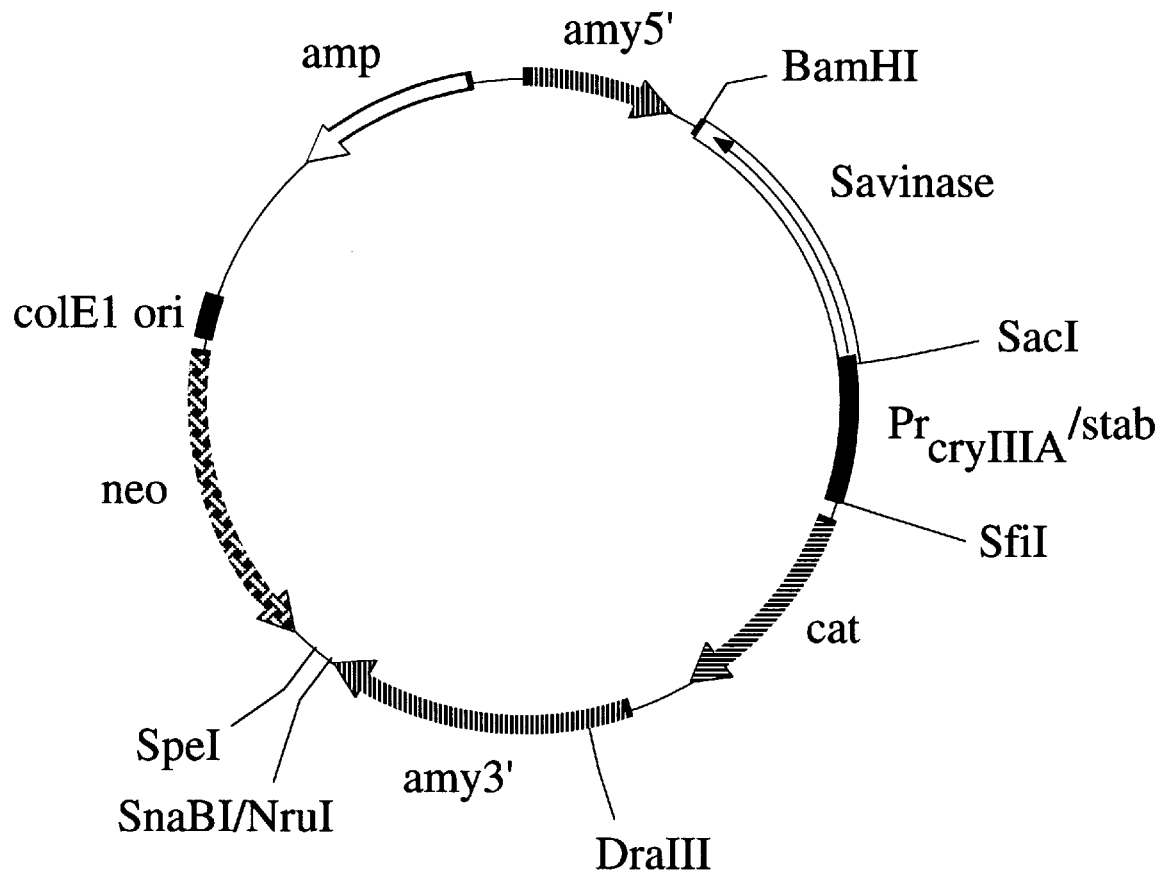

The introduction of an expression cassette, contained in pDG268MCS or a pDG268MCSΔ derivative, into the chromosome of a Bacillus cell must be confirmed by PCR analysis since there is no way of distinguishing whether the introduction into the chromosome is a result of a double (desired) versus a single cross-over event. In order to alleviate this problem, pDG268MCSΔneo-Pr$_{cryIIIA}$/cryIIIAstab/SAV was constructed to contain an antibiotic resistance marker conferring resistance to neomycin, outside of the amyE "front" and amyE "back" regions of homology. A double cross-over results in Cm$^r$, Neo$^s$ transformants whereas a single cross-over results in Cm$^r$, Neo$^r$ transformants allowing the identification of the desired double cross-over events by screening for drug resistances rather than PCR.

pDG268MCSΔneo-Pr$_{cryIIIA}$/cryIIIAstab/SAV was constructed first by digesting pDG268MCSΔ-Pr$_{cryIIIA}$/cryIIIAstab/SAV of Example 2 with BalI and treating with calf intestinal alkaline phosphatase. Plasmid pBEST501 (Itaya et al., 1989, *Nucleic Acids Research* 17:4410) was digested with PstI and NotI, treated with T4 DNA polymerase I to generate blunt ends, and agarose gel purified as described in Example 1 to isolate a fragment harboring the neomycin resistance marker. The gel-purified fragment and BalI-digested plasmid were ligated together and transformed into E. coli DH5α. Ampicillin resistant transformants were selected on LB plates supplemented with 100 μg of ampicillin per ml. The selected transformants were patched onto LB plates supplemented with 50 μg of neomycin per ml to identify neomycin resistant transformants. Plasmid DNA was purified from a few of the neomycin resistant transformants as described in Example 1 and digested with BglII (cuts twice due to the additional BglII site introduced with the neomycin resistance marker) yielding two fragments in the 4 kb range and with BamHI (which is predicted to cut once downstream of the SAVINASE™ protease gene) yielding a fragment of approximately 8 kb. Such a plasmid was identified and designated pDG268MCSΔneo-Pr$_{cryIIIA}$/cryIIIAstab/SAV (FIG. 5).

Example 4
Construction of pHP13ampMCS pHP13-amp, a variant of pHP13 (Haima et al., 1987, *Molecular and General Genetics* 209:335–342), was constructed by digesting pUC9 with AatII, blunting with Klenow fragment and deoxyribonucleotides, and then digesting with HindIII. The larger 2.2 kb fragment was gel-purified with a Qiaex kit (Qiagen, Thousand Oaks, Calif.). pHP13 was digested with HpaI (which cuts within the erythromycin resistance gene), blunted, and then digested with HindIII. The larger 3.0 kb fragment released from pHP13 was then ligated to the 2.1 kb pUC9 fragment containing the pUC9 origin of replication and ampicillin resistance gene. The ligation mixture was transformed into E. coli DH5α. Ampicillin resistant transformants were selected on LB plates supplemented with 100 μg of ampicillin per ml. Plasmid DNA was purified from several transformants as described in Example 1. A plasmid designated pHP13amp was recovered from one of the transformants.

Plasmid pHP13amp was digested with EcoRI and HindIII and the pUC9 MCS was replaced with a new MCS created by annealing 100 pmol of the following polylinker in 50 mM NaCl, 10 mM Tris pH 7.5, and 1 mM EDTA, boiling for 5 minutes, and cooling slowly to room temperature over a 2 hour time period:

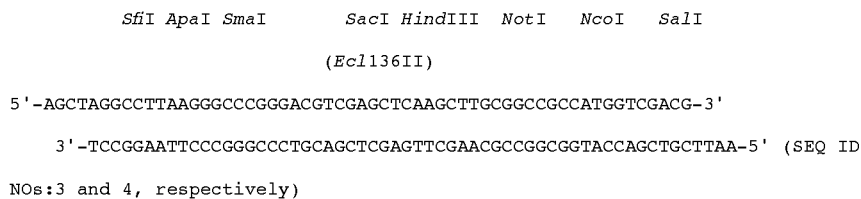

```
           SfiI ApaI SmaI      SacI HindIII  NotI   NcoI   SalI
                              (Ecl136II)
    5'-AGCTAGGCCTTAAGGGCCCGGGACGTCGAGCTCAAGCTTGCGGCCGCCATGGTCGACG-3'
         3'-TCCGGAATTCCCGGGCCCTGCAGCTCGAGTTCGAACGCCGGCGGTACCAGCTGCTTAA-5' (SEQ ID
    NOs:3 and 4, respectively)
```

Figure 6:
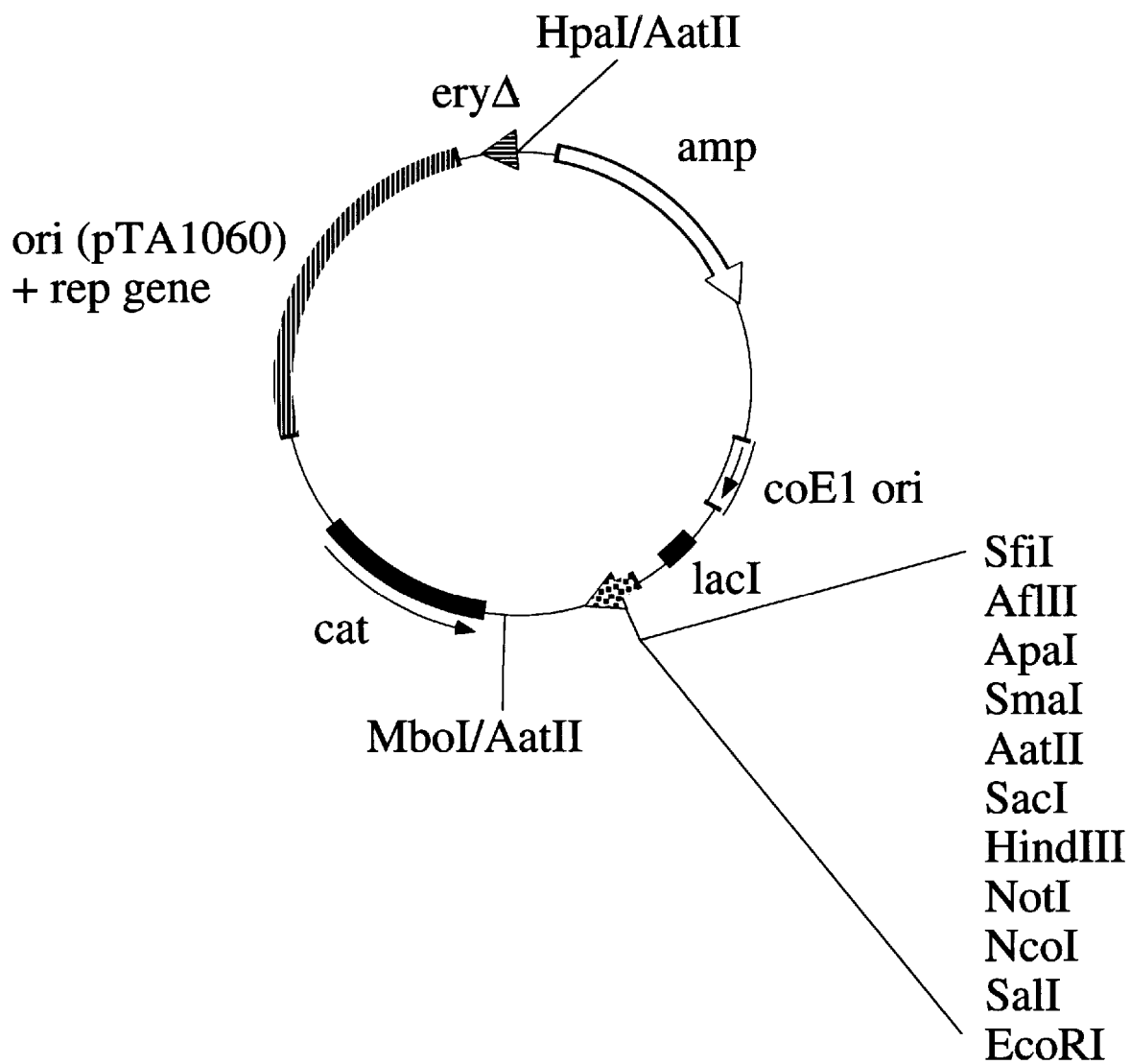

E. coli DH5α was transformed with the ligation mix and ampicillin resistant transformants were selected on LB plates supplemented with 100 μg of ampicillin per ml. Plasmid DNA was purified from several transformants as described in Example 1 and digested with NotI and SacI. Plasmids which were cleaved with these enzymes contained the synthetic polylinker. One such plasmid was identified and designated pHP13amp-MCS (FIG. 6). This plasmid was further verified by DNA sequencing through the polylinker region. DNA sequencing was performed with an Applied Biosystems Model 373A Automated DNA Sequencer (Applied Biosystems, Inc., Foster City, Calif.) according to manufacturer's instructions.

Example 5
Isolation of the SAVINASE™ serine protease gene

Figure 7:
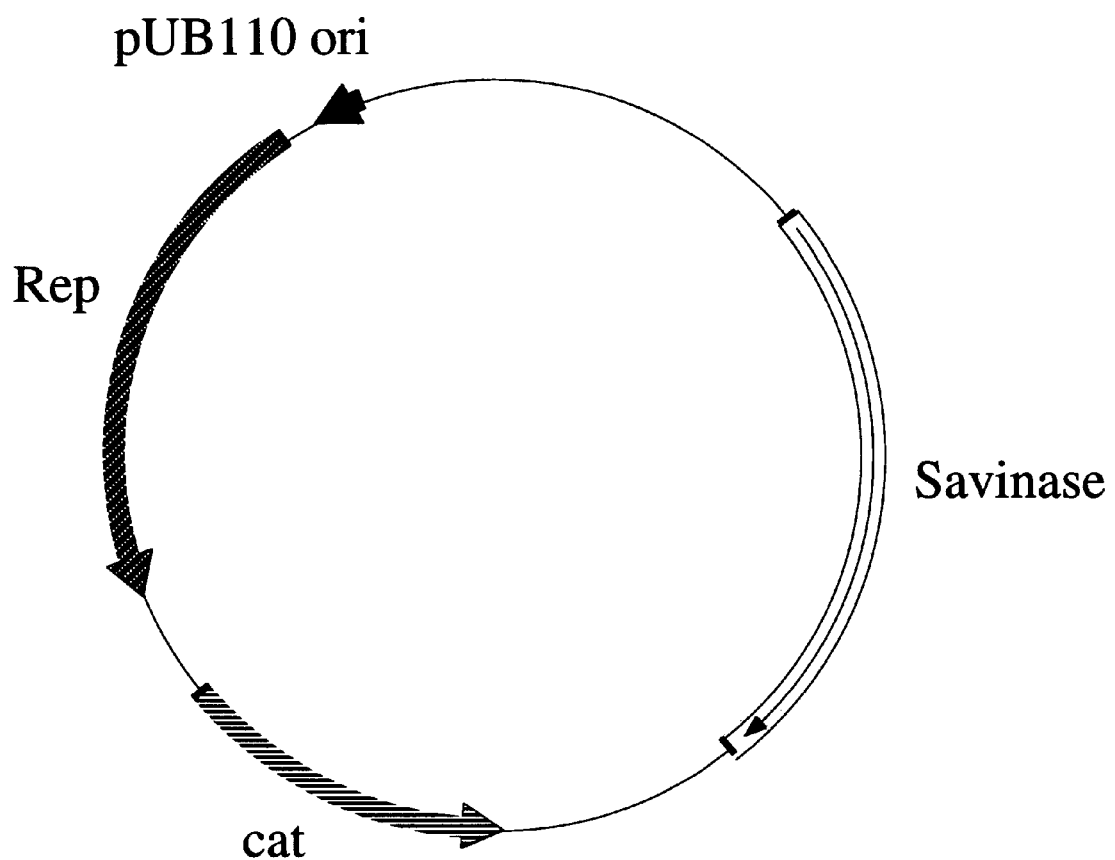

The gene, which encodes a Bacillus serine protease (SAVINASE™, Novo Nordisk A/S, Bagsvǽrd, Denmark), hereinafter referred to as the SAVINASE™ gene, was PCR-amplified using plasmid pSX222 (U.S. Pat. No. 5,621,089) described in FIG. 7 as template DNA and the following two primers (restriction sites are underlined):

```
       ApaI       SacI
5'-CTCCGGGCCCATCTGAGCTCTATAAAAATGAGGAGGG-3'    (SEQ ID NO:5)

BamHI
5'-CCTCGGATCCATACACAAAAAAACGCT-3'              (SEQ ID NO:6)
```

The amplification reaction (100 μl) consisted of the following components: 50 ng of pSX222, 50 pmole of each primer, 1× Taq DNA polymerase Buffer (Boehringer Mannheim, Indianapolis, Ind.), 200 μM each of dATP, dTTP, dGTP, and dCTP, and 2.5 units of Taq DNA polymerase (Perkin-Elmer Corp., Branchburg, N.J.). The amplification conditions were one cycle at 95° C. for 3 minutes, 30 cycles each at 95° C. for 1 minute, 55° C. for 1 minute, and 72° C. for 1.5 minutes, and a final cycle at 72° C. for 5 minutes.

Figure 8:
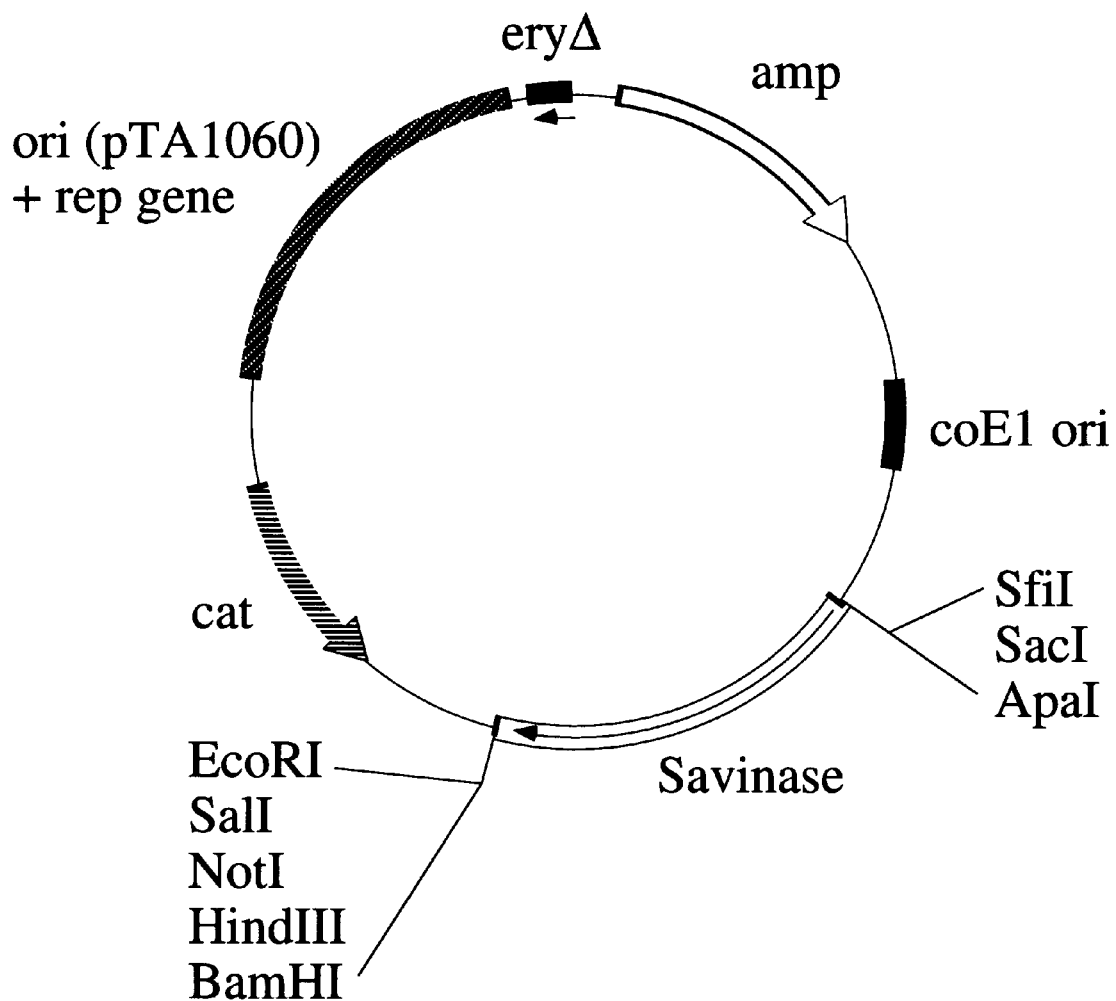

The approximately 1230 bp PCR product was subcloned directly into the pCRII vector (Invitrogen, San Diego, Calif.) according to the manufacturer's instructions. The sequence of the gene was verified by DNA sequencing as described in Example 4 using gene-specific primers. Once verified, the plasmid was digested with BamHI, filled in with Klenow fragment, digested with ApaI, and the fragment harboring the SAVINASE™ gene was then ligated into the ApaI, Ecl136II site of pHP13ampMCS. E. coli DH5α was transformed with this ligation mixture and ampicillin resistant transformants were selected on LB plates supplemented with 100 μg of ampicillin per ml. A plasmid designated pHP13amp-SAV (FIG. 8) was isolated from one of the transformants and verified by DNA sequencing as described in Example 4 using construct-specific primers. The BamHI site was regenerated as a result of this ligation.

Example 6
Construction of an AmyL Promoter-SAVINASE™ Gene Expression Cassette The promoter of the amyL gene, which encodes a *Bacillus licheniformis* alpha-amylase (TERMAMYL™, Novo Nordisk A/S, Bagsvǽrd, Denmark), described in U.S. Pat. No. 5,698,415 was PCR-amplified using plasmid pPL1759 (U.S. Pat. No. 5,698,415) as template DNA, the following two primers (restriction sites are underlined), and GENEAMP® XL PCR Kit (Perkin-Elmer Corp., Branchburg, N.J.) according to the manufacturer's instructions:

```
       SfiI
5'-CCAGGCCTTAAGGGCCGCATGCGTCCTTCTTTGTGCT-3'    (SEQ ID NO:7)

SacI
5'-CCAGAGCTCCTTTCAATGTGTAACATATGA-3'           (SEQ ID NO:8)
```

The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

Figure 9:
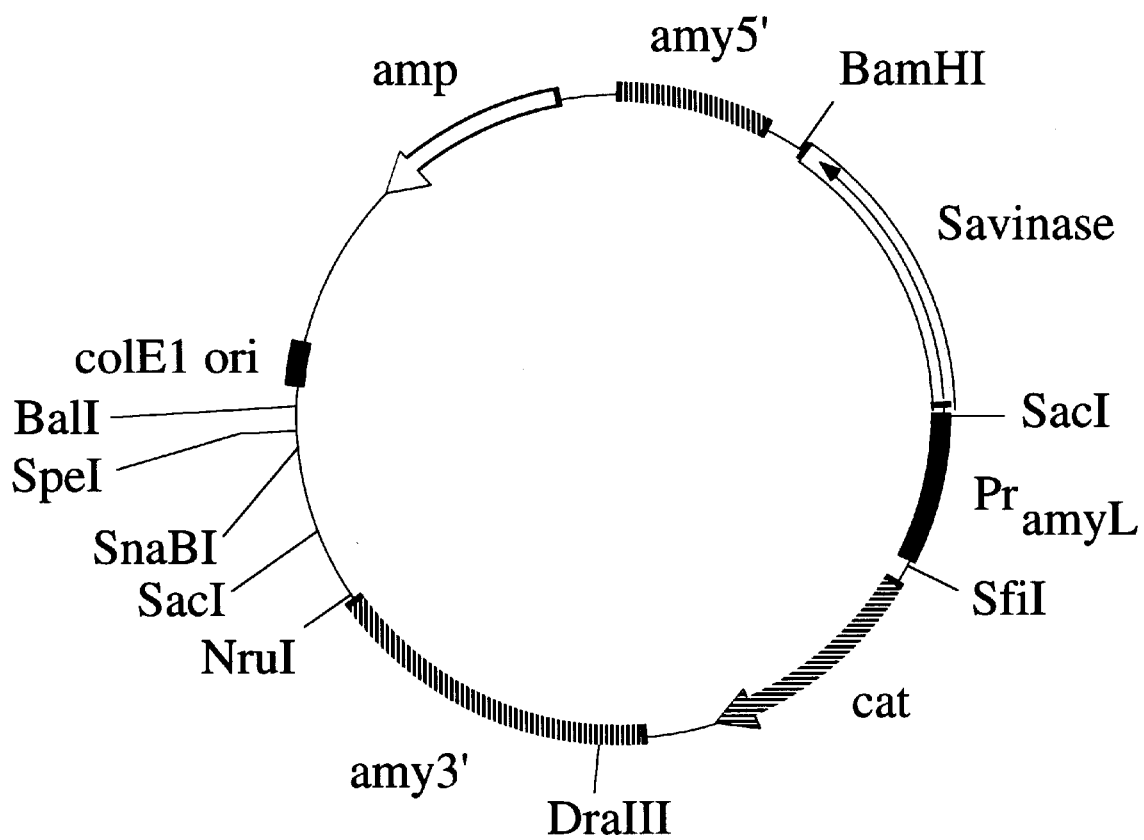

The approximately 620 bp PCR product containing the amyL promoter was ligated with Ecl136II-digested pUC118. E. coli DH5α was transformed with this ligation mixture and ampicillin resistant transformants were selected on LB plates supplemented with 100 μg of ampicillin per ml. A plasmid designated pUC118-Pr$_{amyL}$ was purified from an ampicillin resistant transformant that appeared white in the presence of 5-bromo-4-chloro-3-inodlyl-β-D-galactopyranoside (Sigma, St. Louis, Mo.) and verified by DNA sequencing as described in Example 4, using M13/pUC sequencing primers and amyL-specific primers.

pHP13amp-SAV of Example 5 was digested with SfiI and SacI and purified by gel electrophoresis, as described in Example 1. The approximately 620 bp SfiI-SacI fragment of pUC118-Pr$_{amyL}$ bearing the amyL promoter was isolated by gel electrophoresis, as described in Example 1, and ligated to SfiI/SacI-digested pHP13amp-SAV. E. coli DH5α was transformed with this ligation mixture and ampicillin resistant transformants were selected on LB plates supplemented with 100 μg of ampicillin per ml. A plasmid designated pHP13amp-Pr$_{amyL}$/SAV was purified from one of the ampicillin resistant transformants.

pHP13amp-Pr$_{amyL}$/SAV was digested with SfiI and BamHI and the approximately 1840 bp fragment bearing the Pr$_{amyL}$/SAV cassette was purified as described in Example 1. pDG268MCS was digested with SfiI and BamHI, purified as described in Example 1, and ligated with the Pr$_{amyL}$/SAV SfiI/BamHI fragment. E. coli DH5α was transformed with this ligation and ampicillin resistant transformants were selected on LB plates supplemented with 100 μg of ampicillin per ml. A plasmid designated pDG268MCS-Pr$_{amyL}$/SAV (FIG. 9) was purified from one of the ampicillin resistant transformants.

Example 7
Construction of an amyQ Promoter-SAVINASE™ Gene Expression Cassette The promoter of the amyQ gene which encodes a *Bacillus amyloliquefaciens* alphaamylase (BAN™, Novo Nordisk A/S, Bagsvǽrd, Denmark) was PCR-amplified using plasmid pSX222 as template DNA and the following primers (restriction sites are underlined):

```
                    SfiI
5'-TTTGGCCTTAAGGGCCTGCAATCGATTGTTTGAGAAAAGAAG-3'    (SEQ ID NO:9)

SacI
5'-TTTGAGCTCCATTTTCTTATACAAATTATATTTTACATATCAG-3'   (SEQ ID NO:10)
```

The amplification reaction (100 μl) consisted of the following components: 50 ng of pSX222, 50 pmole of each primer, 1× Taq DNA polymerase buffer, 200 μM each of dATP, dTTP, dGTP, and dCTP, and 2.5 units of Taq DNA polymerase. The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

Figure 10:
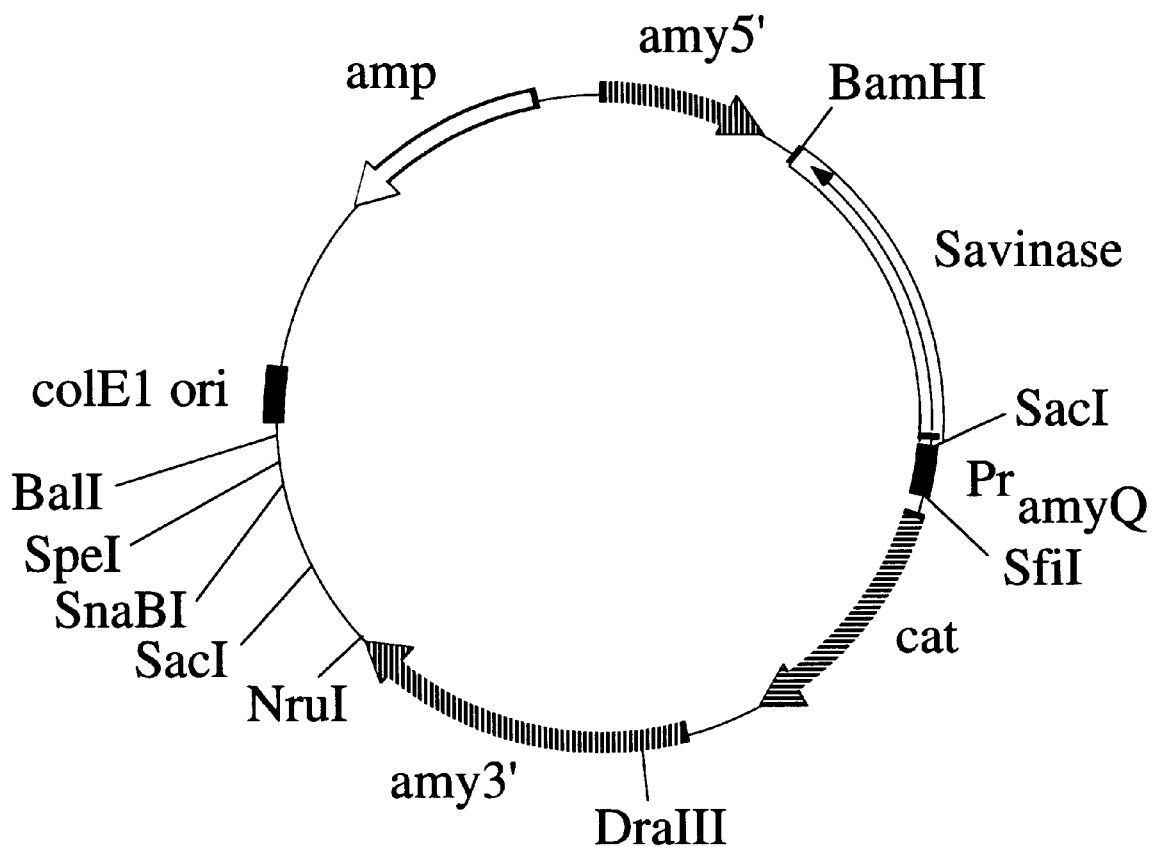

The approximately 185 bp PCR product was subcloned directly into the pCRII vector according to the manufacturer's instructions and verified by DNA sequencing as described in Example 4 yielding pCRII-Pr$_{amyQ}$. The approximately 185 bp SfiI-SacI fragment of pCRII-Pr$_{amyQ}$ bearing the amyQ promoter was isolated by gel electrophoresis, as described in Example 1, and ligated to SfiI/SacI-digested pHP13 amp-SAV (Example 6). *E. coli* DH5α was transformed with this ligation and ampicillin resistant transformants were selected on LB plates supplemented with 100 μg of ampicillin per ml. A plasmid designated pHP13amp-Pr$_{amyQ}$/SAV was purified from one of the ampicillin resistant transformants.

pHP13amp-Pr$_{amyQ}$/SAV was digested with SfiI and BamHI, and the approximately 1400 bp fragment bearing the Pr$_{amyQ}$/SAV expression cassette was purified as described in Example 1. The SfiI-BamHI fragment was then ligated into SfiI-BamHI digested pDG268MCS (Example 6). *E. coli* DH5α was transformed with this ligation mixture and ampicillin resistant transformants were selected on LB plates supplemented with 100 μg of ampicillin per ml. A plasmid designated pDG268MCS-Pr$_{amyQ}$/SAV (FIG. 10) was purified from one of the ampicillin resistant transformants.

Example 8
Construction of pUC18-Pr$_{cryIIIA}$/cryIIIAstab/cryIIIA

The promoter of the cryIIIA gene which encodes a *Bacillus thuringiensis* subsp. *tenebrionis* coleopteran crystal protein CryIIIA was PCR amplified from chromosomal DNA isolated according to Pitcher et al., 1989, *Letters in Applied Microbiology* 8:151–156 from the *Bacillus thuringiensis* subsp. *tenebrionis* strain NB125 described in WO 95/02695 using the following primers:

```
       SmaI
5'-GAGACCCGGGAGCTTTCAGTGAAGTACGTG-3'  (SEQ ID NO:11)

5'-GGGGCGTTACAATTCAAAG-3'             (SEQ ID NO:12)
```

The amplification reaction (100 μl) consisted of the following components: 50 ng of NB125 chromosomal DNA, 50 pmole of each primer, 1×Pfu polymerase buffer (Stratagene Cloning Systems, La Jolla, Calif.), 2.5 μM each of dATP, dTTP, dGTP, and dCTP, and 1.0 unit of Pfu polymerase (Stratagene Cloning Systems, La Jolla, Calif.). The amplification conditions were one cycle at 95° C. for 3 minutes; 30 cycles each at 95° C. for 1 minute, 50° C. for 1 minute, and 72° C. for 1.5 minutes; and a final cycle at 72° C. for 5 minutes. The approximately 1000 bp PCR product was digested with SmaI and HindIII and ligated into the SmaI/HindIII site of pUC18. *E. coli* DH5α was transformed with this ligation mixture and ampicillin resistant transformants were selected on LB plates supplemented with 100 μg of ampicillin per ml. A plasmid designated pUC18-Pr$_{cryIIIA}$ was isolated from one of the ampicillin resistant transformants.

Figure 11:
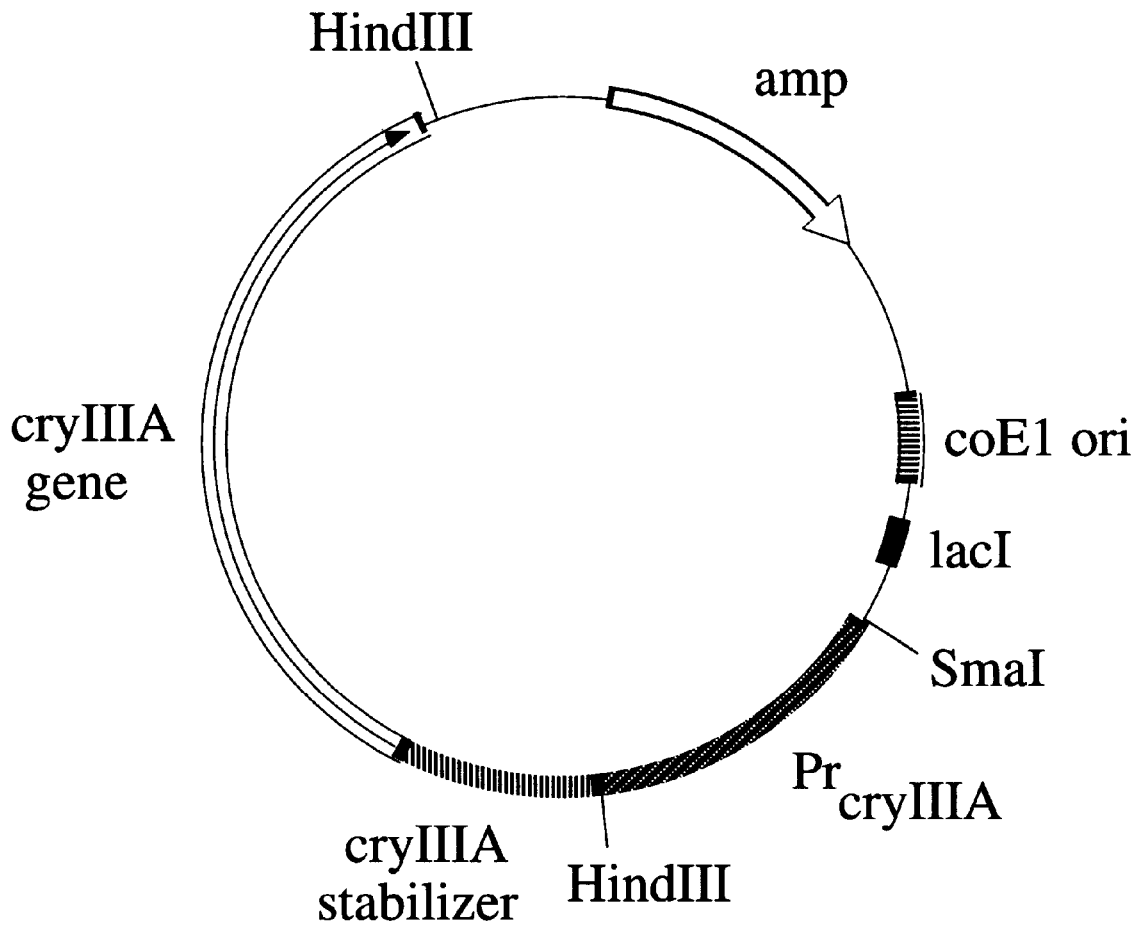

Plasmid pUC118-cryIIIA (WO 95/02695) was digested with HindIII and the approximately 3000 bp HindIII fragment harboring the cryIIIA gene and mRNA stabilizing sequence was gel-purified as described in Example 1. This fragment was ligated into the HindIII site of pUC18-Pr$_{cryIIIA}$. *E. coli* DH5α was transformed with this ligation mixture and ampicillin resistant transformants were selected on LB plates supplemented with 100 μg of ampicillin per ml. A plasmid designated pUC18-Pr$_{cryIIIA}$/cryIIIAstab/cryIIIA (FIG. 11) was isolated from one of the ampicillin resistant transformants. The correct orientation of the fragment was confirmed by digesting the plasmid with EcoRI.

Example 9
Construction of a cryIIIA Promoter-cryIIIA mRNA Stabilizer-SAVINASE™ Gene Expression Cassette The promoter of the cryIIIA gene and the cryIIIA mRNA stabilizing sequence were PCR amplified using plasmid pUC18-Pr$_{cryIIIA}$/cryIIIAstab/cryIIIA as DNA template and the two primers (restriction sites are underlined) described below:

```
       ApaI
5'-GGGCCCTCGAAACGTAAGATGAAACCT-3'    (SEQ ID NO:13)

SacI
5'-GAGCTCCATAATACATAATTTTCAAACTG-3'  (SEQ ID NO:14)
```

The amplification reaction (100 μl) consisted of the following components: 50 ng of pUC18-Pr$_{cryIIIA}$/cryIIIAstab, 50 pmole of each primer, 1× Taq polymerase buffer, 2.5 μM each of dATP, dTTP, dGTP, and dCTP, and 1.0 unit of Taq polymerase. The amplification conditions were one cycle at 95° C. for 3 minutes; 30 cycles each at 95° C. for 1 minute, for 1 minute, and 72° C. for 1.5 minutes; and a final cycle at 72° C. for 5 minutes.

The approximately 630 bp PCR product was cloned in the pCRII vector according to the manufacturer's instructions, yielding plasmid pCRII-Pr$_{cryIIIA}$/cryIIIAstab, which was verified by DNA sequencing as described in Example 4, using M13 sequencing primers and cryIIIA-specific primers.

The approximately 630 bp SfiI-SacI fragment of pCRII-Pr$_{cryIIIA}$/cryIIIAstab bearing the cryIIIA promoter (Pr$_{cryIIIA}$) with mRNA stabilizer sequence was isolated by gel electrophoresis, as described in Example 1, and ligated to SfiI/SacI-digested pHP13amp-SAV (Example 6). *E. coli* DH5α was transformed with this ligation mixture and ampicillin resistant transformants were selected on LB plates supplemented with 100 μg of ampicillin per ml. A plasmid designated pDG268MCS-Pr$_{cryIIIA}$/cryIIIAstab/SAV (FIG. 12) was purified from one of the ampicillin resistant transformants.

Example 10
Construction of a cryIIIA Promoter-SAVINASE™ Gene Expression Cassette pDG268Δneo-Pr$_{cryIIIA}$/SAV was constructed as follows. A fragment of approximately 1640 bp of pDG268Δneo-Pr$_{cryIIIA}$/cryIIIAstab/SAV of Example 3 ranging from the DraIII site to 6 nucleotides downstream of the cryIIIA transcription start site was PCR-amplified using plasmid pDG268MCSΔneo-Pr$_{cryIIIA}$/cryIIIAstab/SAV as DNA template and the following two primers (restriction sites are underlined):

```
        DraIII
5'-CAGCCATCACATTGTGAAATC-3'    (SEQ ID NO:15)

SacI
5'-GAGCTCTATCTTTAATTAAGCTT-3'  (SEQ ID NO:16)
```

Figure 13:
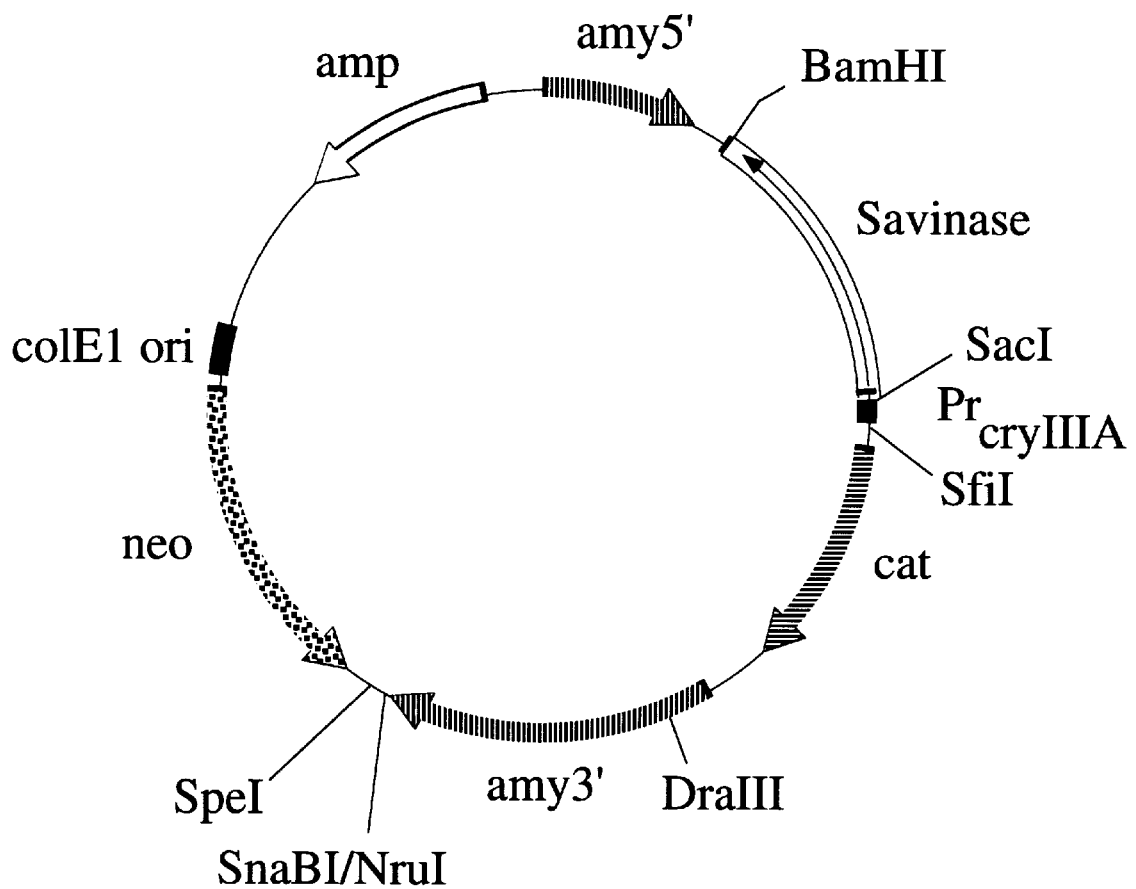

The amplification reaction (50 μl) consisted of the following components: 50 ng of pDG268MCSΔneo-Pr$_{cryIIIA}$/cryIIIAstab/SAV, 50 pmole of each primer, 1× Taq polymerase Buffer, 200 μM each of dATP, dTTP, dGTP, and dCTP, and 1.25 unit of Amplitaq® Gold DNA polymerase (Perkin-Elmer Corporation, Norwalk, Conn.). The amplification conditions were one cycle at 95° C. for 9 minutes; 30 cycles of 95° C. for 1 minute, 55° C. for 1 minute, and 72° C. for 1.5 minutes; and a final cycle at 72° C. for 3 minutes. The PCR product was cloned directly into pCR2.1 using the TOPO-TA Cloning Kit (Invitrogen, San Diego, Calif.) according to the manufacturer's instructions yielding pCR2.1-DraIII/Pr$_{cryIIIA}$, which was verified by DNA sequencing as described in Example 4.

pDG268MCSΔneo-Pr/Pr$_{cryIIIA}$/cryIIIAstab/SAV (see Example 12) was digested with DraIII and SacI to remove the Pr$_{amyL}$/Pr$_{cryIIIA}$/cryIIIAstab tandem promoter and part of the vector, and the approximately 6440 bp vector fragment was isolated by gel electrophoresis, as described in Example 1. The approximately 1640 bp DraIII/SacI fragment of pCR2.1DraIII/Pr$_{cryIIIA}$ was isolated and ligated with the DraIII/SacI-cut vector. E. coli DH5α was transformed with this ligation mixture and ampicillin resistant transformants were selected on LB plates supplemented with 100 μg of ampicillin per ml. A plasmid designated pDG268MCSΔneo-Pr$_{cryIIIA}$/SAV (FIG. 13) was purified from one of the ampicillin resistant transformants.

Example 11
Construction of an amyL Promoter-cryIIIA mRNA Stabilizer-SAVINASE™ Gene Expression Cassette The cryIIIA mRNA stabilizer sequence was PCR-amplified using plasmid pUC18-Pr$_{cryIIIA}$/cryIIIAstab/cryIIIA of Example 8 as DNA template and the following two primers (SacI restriction sites are underlined):

5'-GAGCTCGAACTTGTTCATGTGAA-3' (SEQ ID NO:17)
5'-GAGCTCATAATACATAATTTTCA-3' (SEQ ID NO:18)

The amplification reaction (100 μl) consisted of the following components: 50 ng of pUC18-Pr$_{cryIIIA}$/cryIIIAstab/cryIIIA, 50 pmole of each primer, 1× Taq DNA polymerase Buffer, 200 μM each of dATP, dTTP, dGTP, and dCTP, and 2.5 units of Taq DNA polymerase. The amplification conditions were one cycle at 95° C. for 3 minutes, 30 cycles each at 95° C. for 1 minute, 55° C. for 1 minute, and 72° C. for 1.5 minutes, and a final cycle at 72° C. for 5 minutes. The approximately 360 bp PCR product was subcloned directly into the pCRII vector according to the manufacturer's instructions and confirmed by DNA sequencing, as described in Example 4, using construct specific primers.

Figure 14:
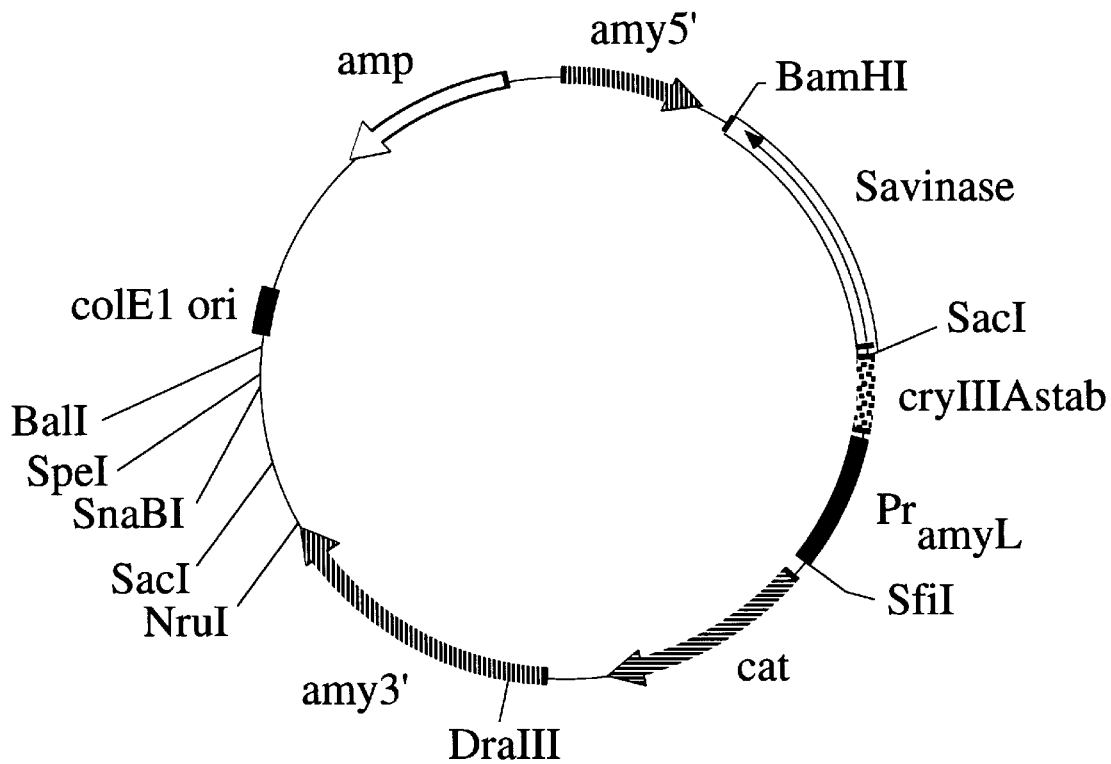

The resulting plasmid designated pCRII-cryIIIAstab was digested with SacI and the fragment harboring the cryIIIA mRNA stabilizer sequence was purified by agarose gel electrophoresis as described in Example 1. Plasmid pHP13amp-Pr$_{amyL}$/SAV of Example 6 was digested with SacI and treated with calf intestine alkaline phosphatase (CIP) to remove the 5' phosphate groups. The purified fragment containing the stabilizer sequence and the CIP-treated plasmid were then ligated together. E. coli DH5α was transformed with this ligation mixture and ampicillin resistant transformants were selected on LB plates supplemented with 100 μg of ampicillin per ml. Plasmid DNA was isolated from several transformants and digested with SacI to identify those which contained the mRNA stabilizer sequence. Once these were identified, the orientation of the fragment was determined by digesting the plasmid DNA with XmnI. A plasmid containing the cryIIIA stabilizing sequence in the correct orientation was identified and designated pHP13amp-Pr$_{amyL}$/cryIIIAstab/SAV.

pHP13amp-Pr$_{amyL}$/cryIIIAstab/SAV was digested with SfiI and BamHI and the fragment harboring the expression cassette was ligated into the SfiI-BamHI site of pDG268-MCS to produce pDG268MCS-Pr$_{amyL}$/cryIIIAstab/SAV (FIG. 14).

Example 12
Construction of a Tandem amyL-cryIIIA Promoter-cryIIIA mRNA Stabilizer-SAVINASE™ Gene Expression Cassette Plasmid pDG268MCSΔneo-Pr$_{cryIIIA}$/cryIIIAstab/SAV of Example 3 was digested with SfiI, blunt-ended with T4 polymerase I, and then digested with DraIII. The digest was separated by agarose gel electrophoresis and the vector fragment of approximately 7010 bp was excised from the gel and the DNA extracted as described in Example 1.

pDG268MCS-Pr$_{amyL}$/SAV of Example 6 was digested with Ecl136II and DraIII. The digest was separated by agarose gel electrophoresis, the promoter fragment of approximately 2150 bp was excised from the gel, and the DNA was extracted as described in Example 1.

Figure 15:
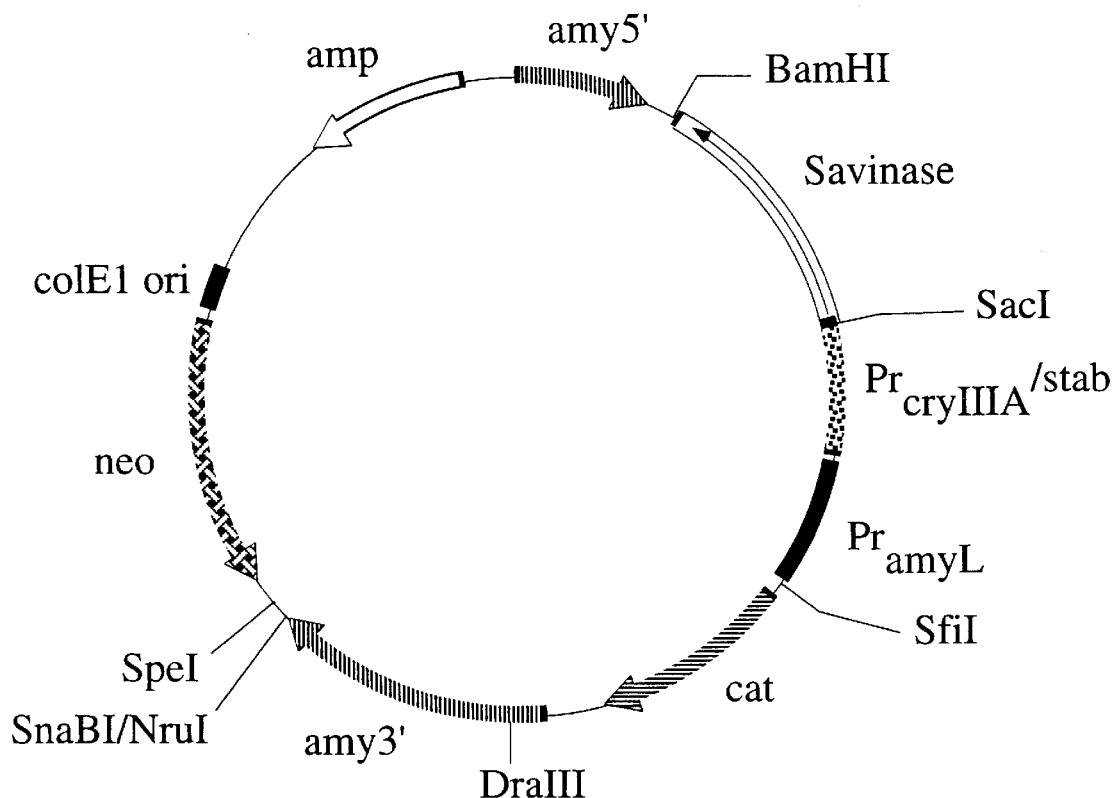

The purified DNAs were ligated together and transformed into E. coli DH5α. Ampicillin resistant transformants were selected on LB plates supplemented with 100 μg of ampicillin per ml. A plasmid designated pDG268MCSΔneo-Pr$_{amyL}$/Pr$_{cryIIIA}$/cryIIIAstab/SAV (FIG. 15) was isolated from one of the transformants and verified by digesting with NcoI followed by agarose gel electrophoresis.

Figure 16:
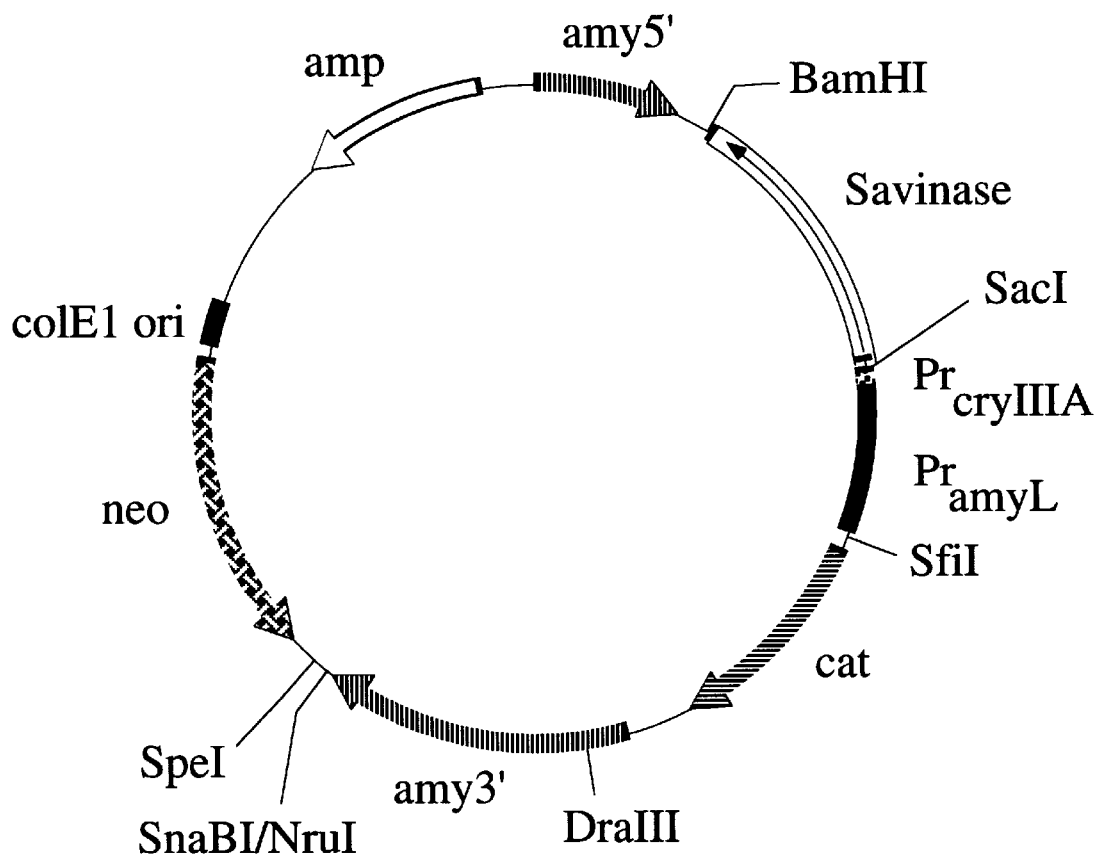

Example 13
Construction of a Tandem amyL-cryIIIA Promoter-SAVINASE™ Gene Expression Cassette pDG268MCSΔneo-Pr$_{cryIIIA}$/SAV of Example 10 was digested with PacI and DraIII, and the approximately 6450 bp vector fragment was isolated by gel electrophoresis, as described in Example 1. The approximately 2230 bp PacI-DraIII fragment of pDG268MCSΔneo-Pr$_{amyL}$/Pr$_{cryIIIA}$/cryIIIAstab/SAV of Example 12 bearing Pr$_{amyL}$ and Pr$_{cryIIIA}$ was isolated by gel electrophoresis, as described in Example 1, and ligated with the vector fragment. E. coli DH5α was transformed with this ligation mixture and ampicillin resistant transformants were selected on LB plates supplemented with 100 μg of ampicillin per ml. A plasmid designated pDG268MCSΔneo-Pr$_{amyL}$/Pr$_{cryIIIA}$/SAV (FIG. 16) was purified from one of the ampicillin resistant transformants.

Example 14
Construction of an amyQ Promoter-cryIIIA Stabilizer-SAVINASE™ Gene Expression Cassette pDG268-Pr$_{amyQ}$/SAV of Example 6 was digested with SfiI and BamHI and the approximately 1400 bp bearing the Pr$_{amyQ}$/SAV cassette was isolated by gel electrophoresis, as described in Example 1. pDG268MCSΔneo-Pr$_{cryIIIA}$/cryIIIAstab/SAV of Example 3 was digested with SfiI and BamHI and the approximately 6780 bp vector fragment was isolated by gel electrophoresis, as described in Example 1. The purified fragments were ligated together, E. coli DH5α was transformed with the ligation, and ampicillin resistant transformants were selected on LB plates supplemented with 100 µg of ampicillin per ml. A plasmid designated pDG268MCSΔneo-Pr$_{amyQ}$/SAV was purified from one of the ampicillin resistant transformants and verified by digestion with NcoI followed by gel electrophoresis.

pDG268MCSΔneo-Pr$_{amyQ}$/cryIIIAstab/SAV was constructed first by digesting pDG268MCSΔneo-Pr$_{amyQ}$/SAV with SacI and treating with calf intestine alkaline phosphatase to remove the 5' phosphate groups. The approximately 360 bp SacI fragment of pDG268MCS-Pr$_{amyL}$/cryIIIAstab/SAV of Example 11 bearing the cryIIIA leader was gelpurified as described in Example 1 and ligated with SacI-cut, dephosphorylated pDG268MCSΔneo-Pr$_{amyQ}$/SAV.

Figure 17:
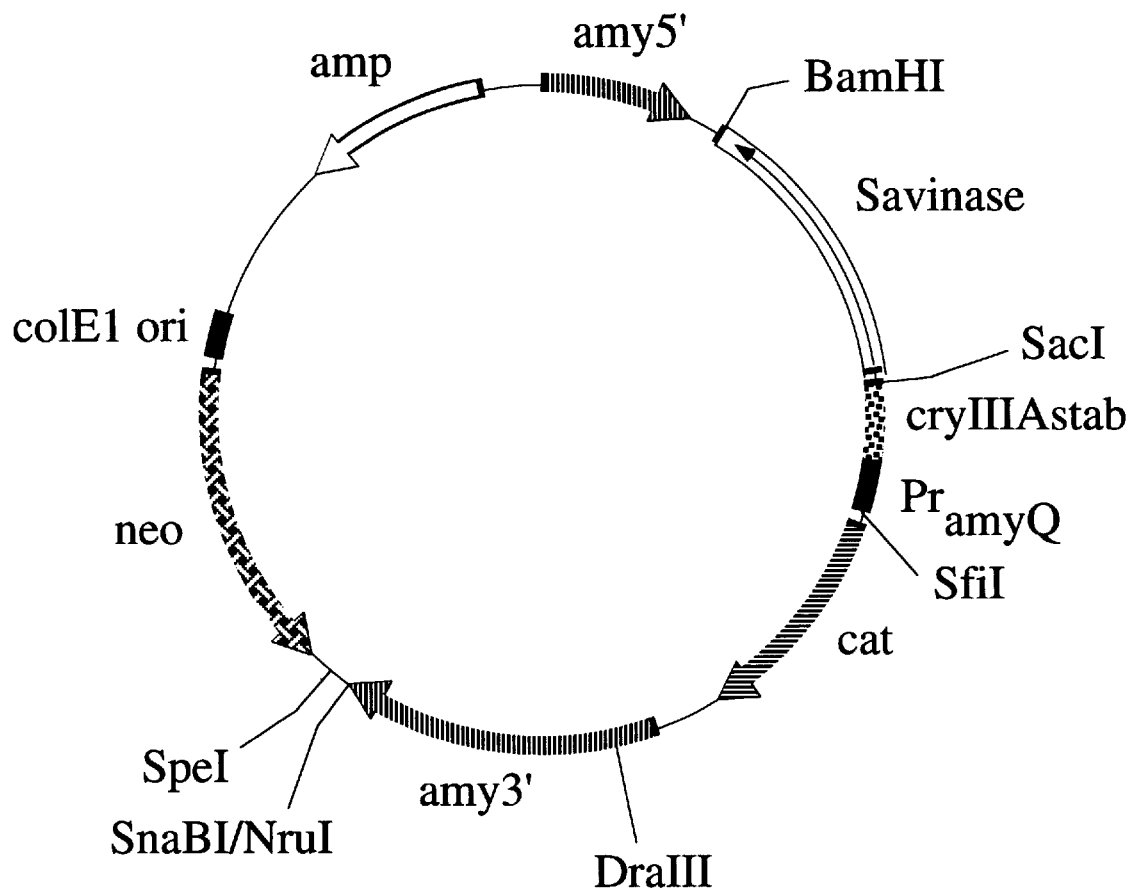

E. coli DH5α was transformed with this ligation mixture and ampicillin resistant transformants were selected on LB plates supplemented with 100 µg of ampicillin per ml. Plasmid DNA was isolated from several transformants and digested with SacI to identify those which contained the stabilizer sequence. Once these were identified, the orientation of the fragment was determined by digesting the plasmid DNA with XmnI. A plasmid containing the cryIIIA mRNA stabilizing sequence in the correct orientation was identified and designated pDG268MCSΔneo-Pr$_{amyQ}$/cryIIIAstab/SAV (FIG. 17).

Example 15
Construction of a Tandem amyQ-cryIIIA Promoter-cryIIIA mRNA Stabilizer-SAVINASE™ Gene Expression Cassette Plasmid pDG268MCS-Pr$_{cryIIIA}$/cryIIIAstab/SAV of Example 9 was digested with SfiI, blunt-ended with T4 polymerase I, and then digested with DraIII. The digest was subjected to agarose gel electrophoresis and the vector fragment of approximately 6360 bp was excised from the gel and the DNA extracted as described in Example 1.

Plasmid pDG268MCS-Pr$_{amyQ}$/SAV of Example 6 was digested with SacI, blunt-ended with T4 DNA polymerase I, digested with DraIII. The digest was subjected to agarose gel electrophoresis and the promoter fragment of approximately 1710 bp was excised from the gel and the DNA extracted as described in Example 1.

Figure 18:
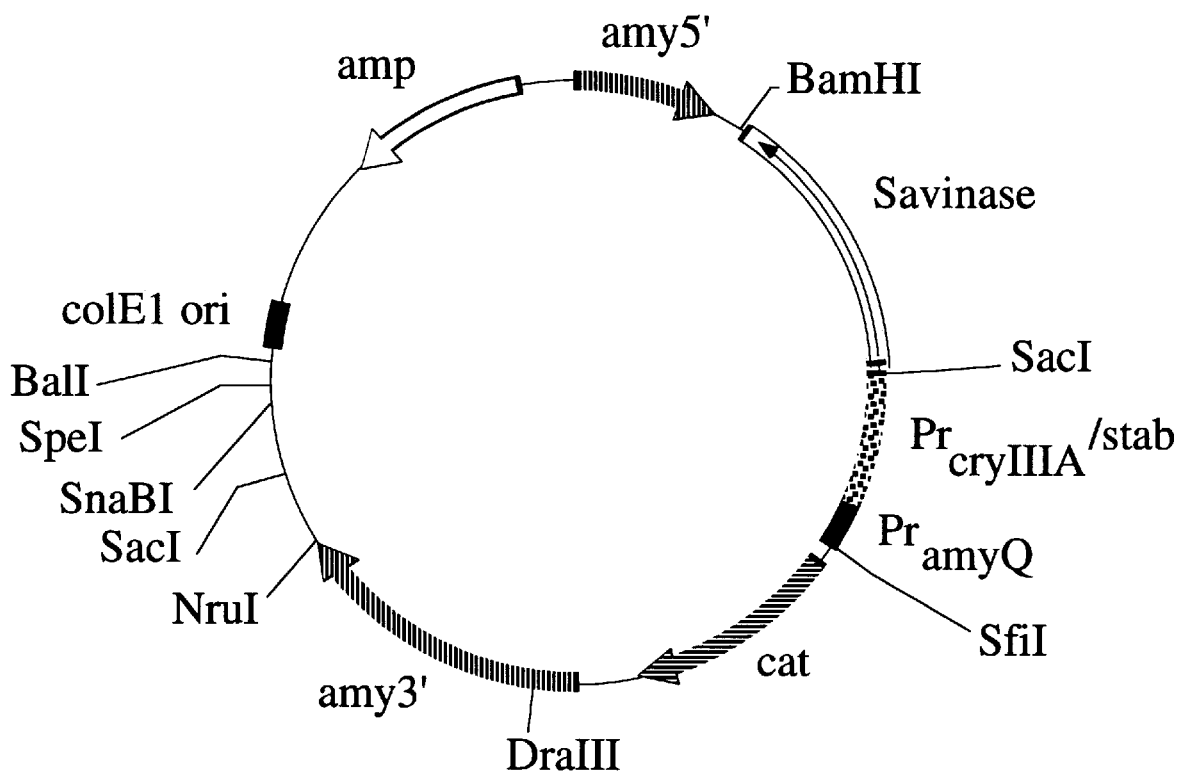

Purified DNAs were ligated together and transformed in E. coli DH5α cells. Ampicillin resistant transformants were selected on LB plates supplemented with 100 µg of ampicillin per ml. A plasmid designated pDG268MCS-Pr$_{amyQ}$/Pr$_{cryIIIA}$/cryIIIAstab/SAV (FIG. 18) was isolated from one of the ampicillin resistant transformants. The plasmid structure was verified by digesting with SacI followed by gel-electrophoresis.

Figure 19:
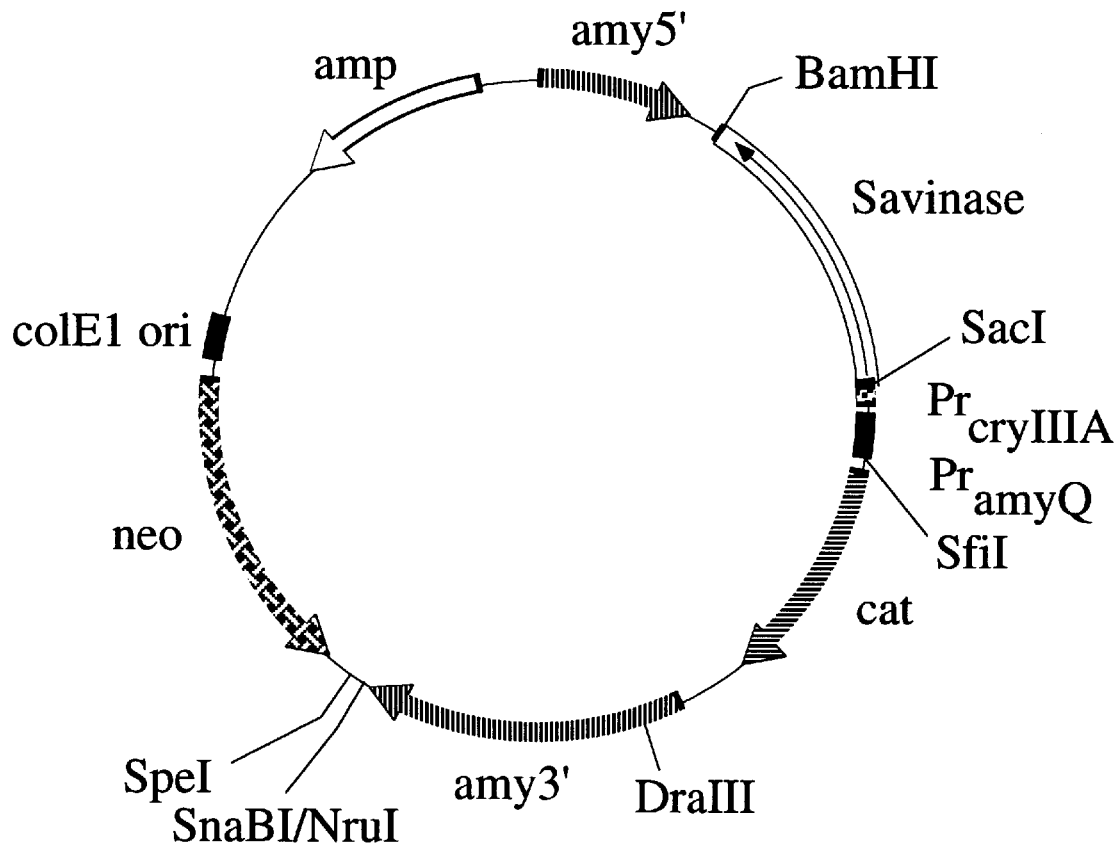

Example 16
Construction of a Tandem amyQ-cryIIIA Promoter-SAVINASE™ Gene Expression Cassette pDG268MCSΔneo-Pr$_{cryIIIA}$/SAV of Example 10 was digested with PacI and DraIII, and the approximately 6450 bp vector fragment was isolated by gel electrophoresis, as described in Example 1. The approximately 1790 bp PacI-DraIII fragment of pDG268MCS-Pr$_{amyQ}$/Pr$_{cryIIIA}$/cryIIIAstab/SAV (Example 15) bearing Pr$_{amyQ}$ and Pr$_{cryIIIA}$ was isolated by gel electrophoresis, as described in Example 1, and ligated with the vector fragment. E. coli DH5α was transformed with this ligation mixture and ampicillin resistant transformants were selected on LB plates supplemented with 100 µg of ampicillin per ml. A plasmid designated pDG268MCSΔneo-Pr$_{amyQ}$/Pr$_{cryIIIA}$/SAV (FIG. 19) was purified from one of the ampicillin resistant transformants.

Example 17
Construction of a cryIIIA Stabilizer-SAVINASE™ Gene Expression Cassette pDG268MCSΔneo-cryIIIAstab/SAV was constructed as follows: pDG268MCSΔneo-Pr$_{cryIIIA}$/cryIIIAstab/SAV of Example 3 was digested with SfiI and treated with T4 DNA polymerase to remove the 3' overhangs. The plasmid was then digested with Asp718. The digest was subjected to agarose gel electrophoresis and the Asp718/blunted SfiI vector fragment of approximately 7540 bp was excised from the gel and the DNA extracted as described in Example 1.

pDG268MCSΔneo-Pr$_{cryIIIA}$/cryIIIAstab/SAV was digested with HindIII and treated with T4 DNA polymerase and dNTPs to fill in the recessed 3' ends. The plasmid was then digested with Asp718. The digest was separated by agarose gel electrophoresis and the fragment of approximately 920 bp containing the truncated cryIIIA promoter (only the "−10" region) and the downstream cryIIIA stabilizing sequence was excised from the gel and the DNA extracted as described in Example 1.

Figure 20:
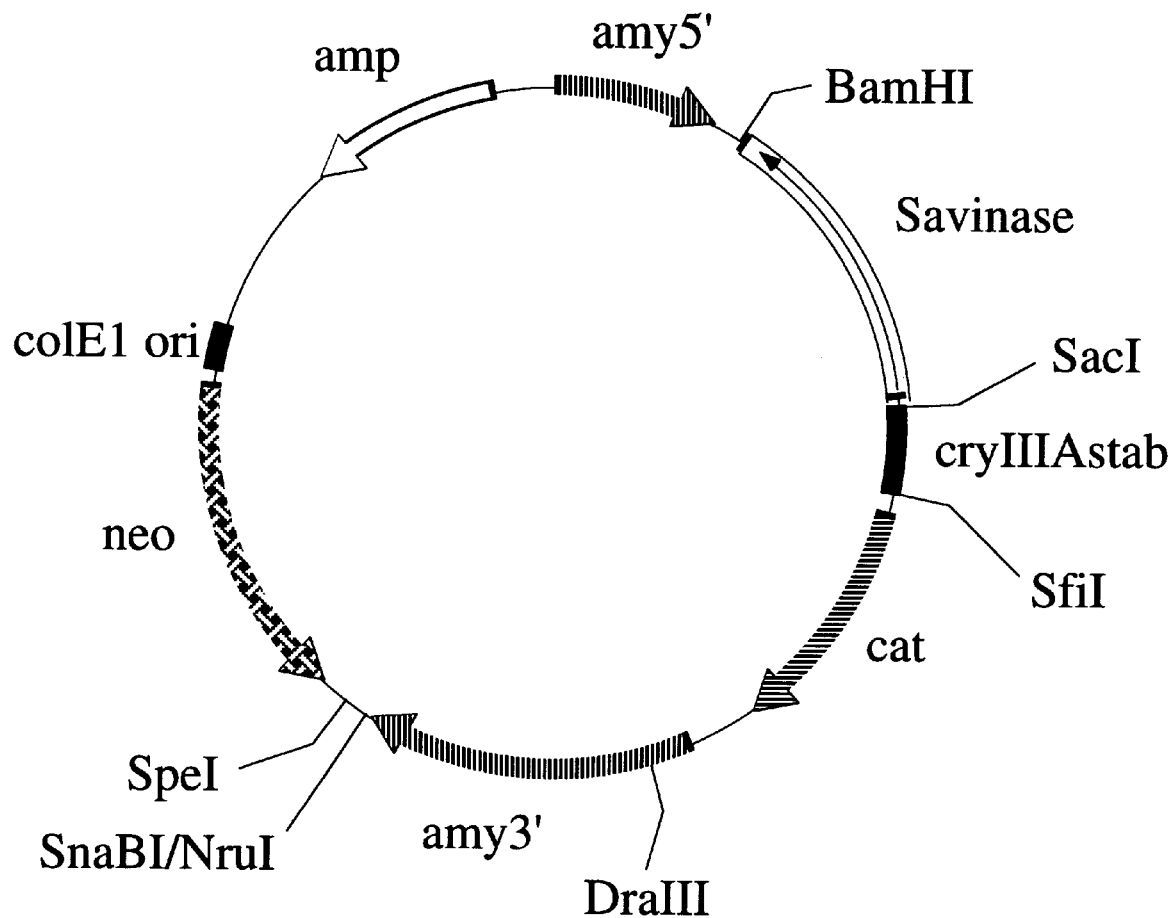

Purified DNAs were ligated together and the ligation mixture was transformed into E. coli DH5α. Ampicillin resistant transformants were selected on LB plates supplemented with 100 µg of ampicillin per ml. A plasmid designated pDG268MCSΔneo-cryIIIAstab/SAV (FIG. 20) was purified from one of the transformants.

Example 18
Copy Number of SAVINASE™ Gene Expression Cassettes in Bacillus subtilis PL1801 spoIIE::Tn917 Integrants The SAVINASE™ gene expression cassettes were each integrated into the amyE locus of Bacillus subtilis strain PL1801 spoIIE::Tn917. Specifically, pDG268MCS derivatives containing the expression cassettes were digested with ScaI to linearize the plasmids. One microgram of linearized plasmid DNA was used to transform competent Bacillus subtilis PL1801 spoIIE::Tn917 to chloramphenicol resistance.

All transformants should contain a single copy of the expression cassette in the amyE locus as a result of a double cross-over event. This was confirmed by DNA dot blot analyses on chromosomal DNA to show the absence of the ampicillin-resistance gene (in integrants derived from pDG268MCS-or pDG268MCSΔ-based plasmids) or by neomycin sensitivity (in integrants derived from pDG268MCSΔneo-based plasmids).

Genomic DNA was isolated from Bacillus subtilis integrants using the QIAGEN bacterial DNA isolation protocol (QIAGEN Inc., Santa Clarita, Calif.). For dot blot analysis, approximately 3 µg genomic DNA were denatured with 400 mM NaOH-10 mM EDTA in a total volume of 10 µl, incubating at room temperature for 10 minutes. One µl of denatured DNA was spotted on a Boehringer-Mannheim positively-charged nylon membrane (Boehringer-Mannheim Corporation, Indianapolis, Ind.) and fixed by UV-crosslinking with a UV STRATALINKER™ 2400 (Stratagene Cloning Systems, La Jolla, Calif.). The membrane was probed with a DNA probe specific to the ampicillin-resistance gene bla, using the Boehringer-Mannheim GENIUS™ System, Version 2.0 (Boehringer-Mannheim Corporation, Indianapolis, Ind.). The blot was developed according to the GENIUS™ protocol using ATTOPHOS® detection reagent (Amersham International, Little Chalfont, UK). The probe was detected using the STORM™ 860 optical scanner and ImageQuant software (Molecular Dynamics, Sunnyvale, Calif.). Inability of the probe to bind to genomic DNA indicated absence of the bla gene, confirming insertion of the plasmid by double crossover.

The bla probe was created by labeling a PCR fragment with digoxigenin-11-dUTP using the Boehringer-Mannheim PCR DIG Probe Synthesis Kit (Boehringer-Mannheim Corporation, Indianapolis, Ind.) The PCR was performed using Amplitaq® Gold DNA polymerase (Perkin-Elmer Corporation, Branchburg, N.J.) and a Robocycler™ 40 thermal cycler (Stratagene Cloning Systems, La Jolla, Calif.) with the following temperature profile: 9 minutes at 95° C.; 30 cycles of 1 minute each at 95° C., 55° C., and 72° C.; and 3 minutes at 72° C. The probe was amplified from pUC118 using the following oligonucleotide primers:
5'-CTATGTGGCGCGGTATTATC-3' (SEQ ID NO:19)
5'-TTCATCCATAGTTGCCTGAC-3' (SEQ ID NO:20)

Once the transformants were confirmed to contain a single copy of the SAVINASE™ expression cassette, single-copy integrants for each expression cassette were analyzed by shake flask analysis.

Example 19

SAVINASE™ Expression in *Bacillus subtilis* PL1801 spoII-E::Tn917

The single-copy integrants of each expression cassette described in Example 19 were grown to mid-log phase in 1 ml of LB broth at 37° C. Then 100 μl of each mid-log phase culture was inoculated into 50 ml of PS-1 medium composed of 10% sucrose, 4% soybean flour, 1% $Na_2PO_4$-$12H_2O$, 0.5% $CaCO_3$, and 0.01% pluronic acid. The cultures were shaken vigorously at 37° C. for 5 days. One ml aliquots were removed on days 3, 4, and 5, centrifuged at 12,000×g for 2 minutes, and 0.5 ml of each supernatant was frozen at −20° C. until all samples were taken. The frozen samples were then thawed and assayed for SAVINASE™ activity using the following protocol to determine relative yields.

The assay for SAVINASE™ activity was performed with casein fluorescein isothiocyanate as substrate. The casein fluorescein isothiocyanate stock solution was prepared according to Twining, 1984, *Analytical Biochemistry* 143: 30–34 and contained 0.5 mg of casein fluorescein isothiocyanate per 100 ml of 50 mM Tris-Cl pH 7.2 buffer. The assay reaction was initiated by the addition of 40 μl of the stock solution mixed 1:1 v/v with 0.25 M borate pH 9.0 buffer to 10 μl of the enzyme sample diluted in 0.25 M borate pH 9.0 buffer as appropriate. The reaction was incubated for 10 minutes at 37° C. and then quenched by adding 150 μl of 5% trichloroacetic acid. The quenched reaction was placed in the cold room for 10 minutes and then centrifuged at top speed for 2 minutes. A 10 μl aliquot of the supernatant was transferred to a test tube containing 2 ml of 0.5 M borate pH 9.0 buffer and mixed well. A 200 μl aliquot of this solution was transferred to a black "U" bottom 96 well plate (Dynatech Laboratories, Inc., Chantilly, Va.) and the fluorescence was measured using a Fluorolite 1000 fluorimeter (Dynatech Laboratories, Inc., Chantilly, Va.) using channel 3 at reference setting 1176 and a lamp voltage at 4.1V. SAVINASE™ activity was calculated by reference to a standard curve generated with a SAVINASE™ standard (Novo Nordisk A/S, BagsvÅrd, Denmark) in the range of 1.8–9.0 NPU (Novo Protease Unit) per ml. The activity of the standard is determined according to Novo Analytical Method AF 220/1-GB available upon request from Novo Nordisk A/S, BagsvÅrd, Denmark.

The results are shown in Table 1. The amyQ, amyL, and cryIIIA promoters (without the stabilizer sequence) were all about equal in strength based on the SAVINASE™ assay results. When the cryIIIA mRNA stabilizer sequence was placed downstream of these promoters their activities increased substantially (at least a 2-fold increase in expression levels). However, when the cryIIIA mRNA stabilizer sequence was included downstream of the tandem promoters, the activities were more than four-fold higher than the single promoters by themselves and about 2-fold higher than the single promoters with the cryIIIA mRNA stabilizer sequence included. When the cryIIIA mRNA stabilizer sequence was used without a promoter, SAVINASE™ expression was very low, indicating that the enhancing effect of the stabilizer sequence was not due to promoter activity within the stabilizer sequence. Therefore, by placing a promoter such as the amyQ or amyL promoter upstream of the cryIIIA promoter and its mRNA stabilizing sequence, a tandem promoter can be created which is far superior activity to any single promoter by itself.

TABLE 1

| Expression Cassette | Relative SAVINASE ™ Activity |
| --- | --- |
| $Pr_{amyL}$/SAV | 90% |
| $Pr_{amyQ}$/SAV | 100% |
| $Pr_{cryIIA}$/cryIIAstab/SAV | 360% |
| $Pr_{cryIIIA}$/SAV | 100% |
| $Pr_{amyL}$/cryIIIAstab/SAV | 230% |
| $Pr_{amyL}$/$Pr_{cryIIIA}$/cryIIIAstab/SAV | 560% |
| $Pr_{amyQ}$/$Pr_{cryIIIA}$/cryIIIAstab/SAV | 560% |
| cryIIIAstab/SAV | 3% |

What is claimed is:

1. A method for producing a polypeptide, comprising:
   (a) cultivating a Bacillus cell in a medium conducive for the production of the polypeptide, wherein the Bacillus cell comprises a nucleic acid construct comprising (i) a tandem promoter in which each promoter sequence of the tandem promoter is operably linked to a single copy of a nucleic acid sequence encoding the polypeptide and (ii) an mRNA processing/stabilizing sequence located downstream of the tandem promoter and upstream of the nucleic acid sequence encoding the polypeptide; and (b) isolating the polypeptide from the cultivation medium.

2. The method of claim 1, wherin the tandem comprises two or more bacterial promoter sequences.

3. The method of claim 2, wherein the two or more bacterial promoter sequences are obtained from one or more Bacillus genes.

4. The method of claim 1, wherein the tandem promoter comprises the amyQ promoter.

5. The method of claim 1, wherein the tandem promoter comprises the amyL promoter.

6. The method of claim 1, wherein the tandem promoter comprises the cryIIIA promoter.

7. The method of claim 1, wherein the tandem promoter comprises the amyQ promoter and the cryIIIA promoter.

8. The method of claim 1, wherein the tandem promoter comprises the amyL promoter and the cryIIIA promoter.

9. The method of claim 1, wherein the tandem promoter comprises two copies of the amyQ promoter.

10. The method of claim 1, wherein the tandem promoter comprises two copies of the amyL promoter.

11. The method of claim 1, wherein the tandem promoter comprises two copies of the cryIIIA promoter.

12. The method of claim 1, wherein the two or more promoter sequences of the tandem promoter simultaneously promote the transcription of the nucleic acid sequence.

13. The method of claim 1, wherein one or more of the two or more promoter sequences of the tandem promoter promote the transcription of the nucleic acid sequence at different stages of growth of the Bacillus cell.

14. The method of claim 1, wherein the mRNA processing/stabilizing sequence is the cryIIIA mRNA processing/stabilizing sequence.

15. The method of claim 1, wherein the mRNA processing/stabilizing sequence is the SP82 mRNA processing/stabilizing sequence.

16. The method of claim 1, wherein the mRNA processing/stabilizing sequence generates mRNA transcripts essentially of the same size.

17. The method of claim 1, wherein the Bacillus cell contains one or more copies of the nucleic acid construct.

18. The method of claim 1, wherein the Bacillus cell contains one copy of the nucleic acid construct.

19. The method of claim 1, wherein the nucleic acid construct further comprises a selectable marker gene.

20. The method of claim 1, wherein the Bacillus cell contains no selectable marker gene.

21. The method of claim 1, wherein the nucleic acid sequence encodes a polypeptide heterologous to the Bacillus cell.

22. The method of claim 1, wherein the polypeptide is a hormone, a hormone variant, an enzyme, a receptor or a portion thereof, an antibody or a portion thereof, or a reporter.

23. The method of claim 22, wherein the enzyme is an oxidoreductase, a transferase, a hydrolase, a lyase, an isomerase, or a ligase.

24. The method of claim 23, wherein the enzyme is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, a pectinolytic enzyme, peroxidase, phytase, polyphenoloxidase, proteolytic enzyme, ribonuclease, transglutaminase, or xylanase.

25. The method of claim 1, wherein the nucleic acid sequence is contained in the chromosome of the Bacillus cell.

26. The method of claim 1, wherein the nucleic acid sequence is contained on an extrachromosomal element.

27. The method of claim 1, wherein the Bacillus host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell.

28. The method of claim 27, wherein the Bacillus cell is a *Bacillus subtilis* cell.

29. A Bacillus cell comprising a nucleic acid construct which comprises (a) a tandem promoter in which each promoter sequence of the tandem promoter is operably linked to a single copy of a nucleic acid sequence encoding a polypeptide, and (b) an mRNA processing/stabilizing sequence located downstream of the tandem promoter and upstream of the nucleic acid sequence encoding the polypeptide.

30. The cell of claim 29, wherein the nucleic acid construct further comprises a selectable marker gene.

31. The cell of claim 29, which contains no selectable marker gene.

32. A method for obtaining a Bacillus host cell, comprising introducing into a Bacillus cell a nucleic acid construct comprising (i) a tandem promoter in which each promoter sequence of the tandem promoter is operably linked to a single copy of a nucleic acid sequence encoding a polypeptide and (ii) an mRNA processing/stabilizing sequence located downstream of the tandem promoter and upstream of the nucleic acid sequence encoding the polypeptide.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 54 base pairs
      (B) TYPE: nucleic acid
      (C) STRANDEDNESS: single (D) TOPOLOGY: linear (xi) SEQUENCE DESCRIPTION: SEQ ID NO:1:

AATTGGCCTT AAGGGCCCGG GACGTCAAGC TTATCGATGC GGATCCGCGG CCGC             54

(2) INFORMATION FOR SEQ ID NO:2:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:2:

CCGGAATTCC CGGGCCCTGC AGTTCGAATA GCTACGCCTA GGCGCCGGCG C                51

(2) INFORMATION FOR SEQ ID NO:3:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:3:

AGCTAGGCCT TAAGGGCCCG GGACGTCGAG CTCAAGCTTG CGGCCGCCAT GGTCGACG         58

(2) INFORMATION FOR SEQ ID NO:4:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:4:

TCCGGAATTC CCGGGCCCTG CAGCTCGAGT TCGAACGCCG GCGGTACCAG CTGCTTAA         58

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:5:

CTCCGGGCCC ATCTGAGCTC TATAAAAATG AGGAGGG                                37

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:6:

CCTCGGATCC ATACACAAAA AAACGCT                                           27

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:7:

CCAGGCCTTA AGGGCCGCAT GCGTCCTTCT TTGTGCT                          37

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

CCAGAGCTCC TTTCAATGTG TAACATATGA                                  30

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:9:

TTTGGCCTTA AGGGCCTGCA ATCGATTGTT TGAGAAAAGA AG                    42

(2) INFORMATION FOR SEQ ID NO:10:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:10:

TTTGAGCTCC ATTTTCTTAT ACAAATTATA TTTTACATAT CAG                   43

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

GAGACCCGGG AGCTTTCAGT GAAGTACGTG                                  30

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:12:

GGGGCGTTAC AATTCAAAG                                              19

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:13:

GGGCCCTCGA AACGTAAGAT GAAACCT                                                              27

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:14:

GAGCTCCATA ATACATAATT TTCAAACTG                                                            29

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

CAGCCATCAC ATTGTGAAAT C                                                                    21

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:16:

GAGCTCTATC TTTAATTAAG CTT                                                                  23

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:17:

GAGCTCGAAC TTGTTCATGT GAA                                                                  23

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:18:

GAGCTCATAA TACATAATTT TCA                                                                  23

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

CTATGTGGCG CGGTATTATC                                                                      20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

| | |
|---|---|
| TTCATCCATA GTTGCCTGAC | 20 |

(2) INFORMATION FOR SEQ ID NO:21:

(i) SEQUENCE CHARACTERISTICS:
        (A) LENGTH: 3050 base pairs
        (B) TYPE: nucleic acid
        (C) STRANDEDNESS: single
        (D) TOPOLOGY: linear (xi) SEQUENCE DESCRIPTION: SEQ ID NO:21:

| | |
|---|---|
| TCGAAACGTA AGATGAAACC TTAGATAAAA GTGCTTTTTT TGTTGCAATT GAAGAATTAT | 60 |
| TAATGTTAAG CTTAATTAAA GATAATATCT TTGAATTGTA ACGCCCCTCA AAAGTAAGAA | 120 |
| CTACAAAAAA AGAATACGTT ATATAGAAAT ATGTTTGAAC CTTCTTCAGA TTACAAATAT | 180 |
| ATTCGGACGG ACTCTACCTC AAATGCTTAT CTAACTATAG AATGACATAC AAGCACAACC | 240 |
| TTGAAAATTT GAAAATATAA CTACCAATGA ACTTGTTCAT GTGAATTATC GCTGTATTTA | 300 |
| ATTTTCTCAA TTCAATATAT AATATGCCAA TACATTGTTA CAAGTAGAAA TTAAGACACC | 360 |
| CTTGATAGCC TTACTATACC TAACATGATG TAGTATTAAA TGAATATGTA AATATATTTA | 420 |
| TGATAAGAAG CGACTTATTT ATAATCATTA CATATTTTTC TATTGGAATG ATTAAGATTC | 480 |
| CAATAGAATA GTGTATAAAT TATTTATCTT GAAAGGAGGG ATGCCTAAAA ACGAAGAACA | 540 |
| TTAAAAACAT ATATTTGCAC CGTCTAATGG ATTTATGAAA AATCATTTTA TCAGTTTGAA | 600 |
| AATTATGTAT TATGATAAGA AAGGGAGGAA GAAAAATGAA TCCGAACAAT CGAAGTGAAC | 660 |
| ATGATACAAT AAAAACTACT GAAAATAATG AGGTGCCAAC TAACCATGTT CAATATCCTT | 720 |
| TAGCGGAAAC TCCAAATCCA ACACTAGAAG ATTTAAATTA TAAAGAGTTT TTAAGAATGA | 780 |
| CTGCAGATAA TAATACGGAA GCACTAGATA GCTCTACAAC AAAAGATGTC ATTCAAAAAG | 840 |
| GCATTTCCGT AGTAGGTGAT CTCCTAGGCG TAGTAGGTTT CCCGTTTGGT GGAGCGCTTG | 900 |
| TTTCGTTTTA TACAAACTTT TTAAATACTA TTTGGCCAAG TGAAGACCCG TGGAAGGCTT | 960 |
| TTATGGAACA AGTAGAAGCA TTGATGGATC AGAAAATAGC TGATTATGCA AAAAATAAAG | 1020 |
| CTCTTGCAGA GTTACAGGGC CTTCAAAATA ATGTCGAAGA TTATGTGAGT GCATTGAGTT | 1080 |
| CATGGCAAAA AAATCCTGTG AGTTCACGAA ATCCACATAG CCAGGGGCGG ATAAGAGAGC | 1140 |
| TGTTTTCTCA AGCAGAAAGT CATTTTCGTA ATTCAATGCC TTCGTTTGCA ATTTCTGGAT | 1200 |
| ACGAGGTTCT ATTTCTAACA ACATATGCAC AAGCTGCCAA CACACATTTA TTTTTACTAA | 1260 |
| AAGACGCTCA AATTTATGGA GAAGAATGGG GATACGAAAA AGAAGATATT GCTGAATTTT | 1320 |
| ATAAAAGACA ACTAAAACTT ACGCAAGAAT ATACTGACCA TTGTGTCAAA TGGTATAATG | 1380 |
| TTGGATTAGA TAAATTAAGA GGTTCATCTT ATGAATCTTG GGTAAACTTT AACCGTTATC | 1440 |
| GCAGAGAGAT GACATTAACA GTATTAGATT TAATTGCACT ATTTCCATTG TATGATGTTC | 1500 |
| GGCTATACCC AAAAGAAGTT AAAACCGAAT TAACAAGAGA CGTTTTAACA GATCCAATTG | 1560 |
| TCGGAGTCAA CAACCTTAGG GGCTATGGAA CAACCTTCTC TAATATAGAA AATTATATTC | 1620 |

```
-continued

GAAAACCACA TCTATTTGAC TATCTGCATA GAATTCAATT TCACACGCGG TTCCAACCAG        1680

GATATTATGG AAATGACTCT TTCAATTATT GGTCCGGTAA TTATGTTTCA ACTAGACCAA        1740

GCATAGGATC AAATGATATA ATCACATCTC CATTCTATGG AAATAAATCC AGTGAACCTG        1800

TACAAAATTT AGAATTTAAT GGAGAAAAAG TCTATAGAGC CGTAGCAAAT ACAAATCTTG        1860

CGGTCTGGCC GTCCGCTGTA TATTCAGGTG TTACAAAAGT GGAATTTAGC CAATATAATG        1920

ATCAAACAGA TGAAGCAAGT ACACAAACGT ACGACTCAAA AAGAAATGTT GGCGCGGTCA        1980

GCTGGGATTC TATCGATCAA TTGCCTCCAG AAACAACAGA TGAACCTCTA GAAAAGGGAT        2040

ATAGCCATCA ACTCAATTAT GTAATGTGCT TTTTAATGCA GGGTAGTAGA GGAACAATCC        2100

CAGTGTTAAC TTGGACACAT AAAAGTGTAG ACTTTTTTAA CATGATTGAT TCGAAAAAAA        2160

TTACACAACT TCCGTTAGTA AAGGCATATA AGTTACAATC TGGTGCTTCC GTTGTCGCAG        2220

GTCCTAGGTT TACAGGAGGA GATATCATTC AATGCACAGA AAATGGAAGT GCGGCAACTA        2280

TTTACGTTAC ACCGGATGTG TCGTACTCTC AAAAATATCG AGCTAGAATT CATTATGCTT        2340

CTACATCTCA GATAACATTT ACACTCAGTT TAGACGGGGC ACCATTTAAT CAATACTATT        2400

TCGATAAAAC GATAAATAAA GGAGACACAT TAACGTATAA TTCATTTAAT TTAGCAAGTT        2460

TCAGCACACC ATTCGAATTA TCAGGGAATA ACTTACAAAT AGGCGTCACA GGATTAAGTG        2520

CTGGAGATAA AGTTTATATA GACAAAATTG AATTTATTCC AGTGAATTAA ATTAACTAGA        2580

AAGTAAAGAA GTAGTGACCA TCTATGATAG TAAGCAAAGG ATAAAAAAAT GAGTTCATAA        2640

AATGAATAAC ATAGTGTTCT TCAACTTTCG CTTTTTGAAG GTAGATGAAG AACACTATTT        2700

TTATTTTCAA AATGAAGGAA GTTTTAAATA TGTAATCATT TAAAGGGAAC AATGAAAGTA        2760

GGAAATAAGT CATTATCTAT AACAAAATAA CATTTTTATA TAGCCAGAAA TGAATTATAA        2820

TATTAATCTT TTCTAAATTG ACGTTTTTCT AAACGTTCTA TAGCTTCAAG ACGCTTAGAA        2880

TCATCAATAT TTGTATACAG AGCTGTTGTT TCCATCGAGT TATGTCCCAT TTGATTCGCT        2940

AATAGAACAA GATCTTTATT TTCGTTATAA TGATTGGTTG CATAAGTATG GCGTAATTTA        3000

TGAGGGCTTT TCTTTTCATC AAAAGCCCTC GTGTATTTCT CTGTAAGCTT                  3050
```